US007700327B2

(12) United States Patent
King et al.

(10) Patent No.: US 7,700,327 B2
(45) Date of Patent: Apr. 20, 2010

(54) RESISTANT STARCH WITH COOKING PROPERTIES SIMILAR TO UNTREATED STARCH

(75) Inventors: Joan M. King, Baton Rouge, LA (US); Siow Ying Tan, Ithaca, NY (US)

(73) Assignee: Board of Supervisors of Louisiana State University and Agricultural and Mechanical College, Baton Rouge, IL (US)

( * ) Notice: Subject to any disclaimer, the term of this patent is extended or adjusted under 35 U.S.C. 154(b) by 701 days.

(21) Appl. No.: 10/936,116

(22) Filed: Sep. 7, 2004

(65) Prior Publication Data

US 2005/0089624 A1 Apr. 28, 2005

Related U.S. Application Data

(60) Provisional application No. 60/501,121, filed on Sep. 8, 2003.

(51) Int. Cl.
*C12P 19/16* (2006.01)
*C12P 1/00* (2006.01)
*C12P 19/14* (2006.01)
*A23G 3/00* (2006.01)
*A21D 13/00* (2006.01)

(52) U.S. Cl. .............................. 435/98; 435/41; 435/99; 426/549; 426/658

(58) Field of Classification Search .................. None
See application file for complete search history.

(56) References Cited

U.S. PATENT DOCUMENTS

| 4,628,031 | A | 12/1986 | Zeikus et al. ................ 435/205 |
| 4,971,723 | A | 11/1990 | Chiu ........................... 516/105 |
| 5,051,271 | A | 9/1991 | Iyengar et al. .............. 426/658 |
| 5,281,276 | A | 1/1994 | Chiu et al. .................... 127/65 |
| 5,395,640 | A * | 3/1995 | Harris et al. ................. 426/573 |
| 5,409,542 | A | 4/1995 | Henley et al. .................. 127/65 |
| 5,480,669 | A | 1/1996 | Zallie et al. .................. 426/549 |
| 5,593,503 | A | 1/1997 | Shi et al. ....................... 127/71 |
| 5,721,127 | A | 2/1998 | Deweer et al. .............. 435/210 |
| 5,849,090 | A | 12/1998 | Haralampu et al. ........... 127/65 |
| 5,902,410 | A | 5/1999 | Chiu et al. ...................... 127/71 |
| 5,962,047 | A | 10/1999 | Gross et al. .................... 426/48 |
| 6,043,229 | A | 3/2000 | Kerlitz et al. .................. 514/60 |
| 6,090,594 | A | 7/2000 | Kettlitz et al. ................. 435/98 |
| 6,303,174 | B1 * | 10/2001 | McNaught et al. .......... 426/549 |
| 6,468,355 | B1 | 10/2002 | Thompson et al. ............ 127/71 |
| 7,045,003 | B2 * | 5/2006 | Klingler et al. .......... 106/206.1 |
| 2003/0054501 | A1 | 3/2003 | Schmiedel et al. .......... 435/101 |

FOREIGN PATENT DOCUMENTS

WO WO 01/21011 A1 * 3/2001

OTHER PUBLICATIONS

Guraya, H.S., et al. "Effect of Enzyme Concentration and Storage Temperature on the Formation of Slowly Digestible Starch from Cooked Debranched Rice Starch", Starch. 2001, 53 (3-4), pp. 131-139.*
Berry, C.S., "Resistant starch: Formation and measurement of starch that survives exhaustive digestion with amylolytic enzymes during the determination of dietary fiber," J. Cereal Sci., vol. 4, pp. 301-314 (1986).
Englyst, H.N. et al., "Classification and measurement of nutritionally important starch fractions," European Journal of Clinical Nutrition, vol. 46 (Suppl. 2), pp. S33-S50 (1992).
Sievert, C. et al., "Enzyme-resistant starch. I. Characterization and evaluation by enzymatic, thermoanalyical and microscropic methods," Cereal Chem., vol. 66, pp. 342-347 (1989).
Yue, P. et al., "Functionality of resistant starch in food applications," Food Australia, vol. 50, pp. 615ff, as reprinted by National Starch & Chemical Company (1998).
Aboubacar, A. et al., "The effects of growth location on US rice starch structure and functionality," Whistler Center for Carbohydrate Research and Dept. of Food Science, Purdue University. West Lafayette, IN 47907-1160 (2002).
Eerlingen, R.C. et al., "Enzyme-resistant starch. IV. Effect of endogenous lipids and added sodium dodecyl sulfate on formation of resistant starch," Cereal Chem., vol. 71(2), pp. 170-177 (1994).
Eliasson, A.C. et al., "Ch 10. Starch: Physicochemical and Functional Aspects," In, *Carbohydrates in Food*, pp. P441-443 (1996).
Fennema, O.R., Ed., 3$^{rd}$ ed, *Food Chemistry*, Ch. 4, "Carbohydrates," Marcel Dekker, Inc. New York, pp. 167-168, 174, 195, 196 (1996).
French, D. et al., "The structural analysis and enzymic synthesis of a pentasaccharide alpha-limit dextrin formed from amylopectin by *Bacillus subtilis* alpha-amylase," Carbohydr. Res., vol. 22, pp. 123-134 (1972).
Jenkins, D.J.A. et al., "Low glycemic index: Lente carbohydrates and physiological effects of altered food frequency," Am. J. Clin. Nutr., vol. 59, p. 706S (1994).
Liang, X.M. et al., "Pasting and Crystalline Property Differences of Commercial and Isolated Rice Starch and Added Amino Acids," Journal of Food Science, vol. 68, pp. 832-838 (2003).

(Continued)

*Primary Examiner*—Christopher R Tate
*Assistant Examiner*—Aaron J Kosar
(74) *Attorney, Agent, or Firm*—Bonnie J. Davis; John H. Runnels

(57) ABSTRACT

A method has been discovered to produce a resistant starch product that retains the same cooking quality as found in untreated rice starch or flour, but has a higher percentage of starch resistant to α-amylase digestion. This method uses a debranching enzyme, e.g., pullulanase, to digest the starch, but does not require pre-treating the starch source prior to enzymatic treatment. This method produced resistant starch from low amylose starches, rice starch (24%) and rice flour (20%). Surprisingly the resistant starch product formed by this method retained the pasting characteristics of the untreated flour or starch, and was heat stable. This method may also be used to produce resistant starch from other botanical sources, e.g., corn, wheat, potato, oat, barley, tapioca, sago, and arrowroot. Resistant starch produced by this method has a variety of uses in food products.

6 Claims, 12 Drawing Sheets

OTHER PUBLICATIONS

Liang, X.M. et al., "Pasting Property Differences of Commercial and Isolated Rice Starch with Added Lipids and β-Cyclodextrin," Cereal Chem., vol. 79, pp. 812-818 (2002).

Manelius, "Enzymatic and Acidic Hydrolysis of Native and Modified Starch Granules," Acta Academiae Aboensis, Ser. B., vol. 60(2), pp. 20-21 (2000).

Panlasigui, L.N. et al., "Rice varieties with similar amylose content differ in starch digestibility and glycemic response in humans," Am. J. Clin. Nutr., vol. 54, pp. 871-7 (1991).

Rashmi, S. et al., "Effect of processing on nutritionally important starch fractions in rice varieties," International Journal of Food Sciences and Nutrition, vol. 54, pp. 27-36 (2003).

Russell, P.L. et al., "Characterization of resistant starch from wheat and maize," J. Cereal Sci., vol. 9, pp. 1-15 (1989).

Sasaki, T. et al., "Effect of Amylose Content on Gelatinization, Retrogradation, and Pasting Properties of Starches from Waxy and Nonwaxy Wheat and Their F1 Seeds," Cereal Chem., vol. 77, pp. 58-63 (2000).

Sievert, C. et al., "Enzyme-resistant starch. II. Differential scanning calorimetry studies on heat-treated starches and enzyme-resistant starch residues," Cereal Chem., vol. 68, pp. 86-91 (1990).

Sievert, D. et al., "Enzyme-resistant starch. II. Differential Scanning Calorimetry Studies on Heat-Treated Starches and Enzyme-Resistant Starch Residues," Cereal Chem., vol. 67(3), pp. 217-221 (1990).

Slade, L. et al., "Starch and sugars as partially-crystalline water-compatible polymer systems," Cereal Food World, vol. 32(9), p. 680 (1987).

Tan, S.Y. et al., "Enzymatic Treatment to form Resistant Rice Starch," a poster presented on Jul. 14, 2003, at the 2003 Annual Meeting of the Institute of Food Technologists, Chicago, Illinois, 1 page.

Tan, S.Y. et al., "Enzymatic treatment to form resistant rice starch," An abstract for the 2003 Annual Meeting of the Institute of Food Technologists, published online Mar. 2003, 1 page.

Tan, S.Y., "Resistant Rice Starch Development," A thesis submitted to the Department of Food Science, Louisiana State University, Aug. 2003, 141 pages.

Thorburn, A.W. et al., "Slowly digested and absorbed carbohydrate in traditional bushfoods: A protective factor against diabetes?" Am. J. Clin. Nutr., vol. 45(1), pp. 98-106 (1987).

Zeng, M. et al., "Sources of variation for starch gelatinization, pasting, and gelation properties in wheat," Cereal Chem., vol. 74, pp. 63-71 (1997).

Lin, L-L. et al., "Improved Elution of Isoamylase Adsorbed on Raw Starch and the Preservation of Purified Enzyme," Letters in Applied Microbiology, vol. 19, pp. 383-385 (1994).

Kimura, Atsuo et al., "Reaction of Enzymes with Starch Granules: Reaction of Isoamylase with Native and Gelatinized Granules," Carbohydrate Res., vol. 287, pp. 255-261 (1996).

* cited by examiner

RESISTANT STARCH WITH COOKING PROPERTIES SIMILAR TO UNTREATED STARCH

The benefit of the filing date of provisional application 60/501,121, filed Sep. 8, 2003, is claimed under 35 U.S.C. §119(e) in the United States, and is claimed under applicable treaties and conventions in all countries.

This invention pertains to a resistant starch produced from a native starch, e.g., rice starch or rice flour, that retains the pasting characteristics of the native starch, and to a new method to produce this resistant starch.

The beneficial effects of resistant starch are well known. However, most methods of producing resistant starch begin with a starch that is at least 40% amylose, usually from corn. These methods usually do not work well with rice starches since even high amylose starch from rice is only about 27% amylose. See, U.S. Pat. No. 6,303,174. Other sources of starch include wheat, oat, barley, tapioca, sago, cassava, potato, and arrowroot.

One advantage to rice is that people who are allergic to wheat often do not have problems with rice. Use of rice as a food ingredient accounts for 22% of domestic rice sales. This use has increased by 3.7%, due to the rising popularity and availability of snacks, frozen dinners, rice pudding, package mixes and candy. Pet food products are also incorporating rice as an ingredient. Even though rice contains only 7 to 8% protein, the protein quality is high and also is high in the essential amino acid, lysine. In contrast, most other grains are deficient in lysine. Rice is approximately 87% carbohydrates, but rice starch contains less amylose than other high amylose grains, e.g., potato and corn. Rice starch consists primarily of amylose and amylopectin.

Starch

Starch is primarily a mixture of two polymers of glucose residues: amylose and amylopectin. In untreated starch, the two polymers are packed into discrete particles (granules). Particle size ranges from 2-100 µm. At 80° C. (175° F.), unmodified starch granules form a paste with very high viscosity, as the starch granules swell and are disrupted. See O. R. Fennema, Ed., $3^{rd}$ ed, *Food Chemistry*, Ch. 4, "Carbohydrates," Marcel Dekker, Inc. New York, pp. 167-168, 174, 195, 196 (1996). When the starch is cooled, retrogradation occurs as amylose recrystallizes. See S. Rashmi et al., "Effect of processing on nutritionally important starch fractions in rice varieties," International Journal of Food Sciences and Nutrition, vol. 54, pp. 27-36 (2003).

Starch is insoluble in cold water and can imbibe water reversibly. When heated in water, starch can undergo gelatinization as starch granules swell. Gelatinization can be irreversible if the starch granules are so disrupted to cause excess starch granule swelling and loss of birefringence and crystallinity (Fennema, 1996). Gelatinization is a process that normally occurs over a temperature range of approximately 10 to 15° C. The gelatinization temperature range for waxy, normal rice starch with about 50% water is in the range of 61-93° C. If this rice starch contains about 20% amylose, it gelatinizes between 60 and 78° C. See D. J. A. Jenkins et al., "Low glycemic index: Lente carbohydrates and physiological effects of altered food frequency," Am. J. Clin. Nutr., vol. 59, p: 706S (1994); and A. W. Thorburn et al., "Slowly digested and absorbed carbohydrate in traditional bushfoods: A protective factor against diabetes?" Am. J. Clin. Nutr., vol. 45(1), pp.: 98-106 (1987). The degree of gelatinization is affected by a number of factors, such as temperature, starch:water ratio, granule type, measurement technique, granule heterogeneity within the starch sample, and actual botanical source of starch. See Fennema, 1996; A. C. Eliasson et al., "Ch 10. Starch: Physicochemical and Functional Aspects," In, *Carbohydrates in Food*, pp. P441-443 (1996); and Z. Ming et al., "Sources of variation for starch gelatinization, pasting, and gelation properties in wheat," Cereal Chem., vol. 74, pp. 63-71 (1997). One method to measure gelatinization temperature is by differential scanning calorimetry (DSC). See Eliasson et al., 1996; Fennema, 1996; C. Sievert et al., "Enzyme-resistant starch. II. Differential scanning calorimetry studies on heat-treated starches and enzyme-resistant starch residues," Cereal Chem., vol. 68, pp. 86-91 (1990); D. Sievert et al., "Enzyme-resistant starch. II. Differential Scanning Calorimetry Studies on Heat-Treated Starches and Enzyme-Resistant Starch Residues," Cereal Chem., vol. 67(3), pp. 217-221 (1990).

Retrogradation of starch occurs as dissolved starch becomes less soluble and more ordered in a crystalline state. (Fennema, 1996) The rate of retrogradation is dependent on the molecular ratio of amylose to amylopectin, the structure of the amylose and amylopectin molecules (source of starch), temperature, starch concentration, and concentrations of other ingredients such as surfactants and salts. In general, retrogradation occurs to a greater extent with higher linear amylose content. Shelf-life and quality of food products can be shortened or decreased due to retrogradation, e.g., bread staling, loss of viscosity and precipitation in soups and sauces. (Fennema, 1996)

When starch is heated past gelatinization in excess water so that the starch granules swell and become totally disrupted, a viscous mass (paste) is formed, a process called pasting. The rapid visco amylograph (RVA) measures the pasting characteristics of starch in rapid visco units (RVU). RVA is unable to measure gelatinization onset because the starch granules are gelatinized before viscosity begins to increase and be detected. See X. M. Liang et al., "Pasting Property Differences of Commercial and Isolated Rice Starch with Added Lipids and β-Cyclodextrin," Cereal Chem., vol. 79, pp. 812-818 (2002). The pasting characteristics determine the cooking properties of the starch and are useful in determining the use in food products. RVA has been used to investigate the pasting effects of lipids and amino acids on rice starch and flour. See Liang et al., 2002; and X. M. Liang et al., "Pasting and Crystalline Property Differences of Commercial and Isolated Rice Starch and Added Amino Acids," Journal of Food Science, vol. 68, pp. 832-838 (2003).

There are three categories of starches based on digestion properties: readily digestible (RDS), slowly digestible (SDS), and resistant starch (RS). Resistant starch is defined as starch that has the ability to survive prolonged incubation with α-amylase and thus passes undigested into the large intestine in humans. See H. N. Englyst et al., "Classification and measurement of nutritionally important starch fractions," European Journal of Clinical Nutrition, vol. 46 (Suppl. 2), pp. S33-S50 (1992); and C. S. Berry, "Resistant starch: Formation and measurement of starch that survives exhaustive digestion with amylolytic enzymes during the determination of dietary fiber," J. Cereal Sci., vol. 4, pp. 301-314 (1986). Resistant starch can be further divided into four subgroups: RS1 which is physically inaccessible starch, RS2 which is food that is often eaten raw or cooked with very little water so that the granular structure is intact, and RS3 as retrograded amylose. (Englyst et al., 1992). RS3 has been characterized as native starch granules that have been gelatinized and retrograded afterwards. (Eerlingen, 1994) As the amylose content in the starch increases, the degree of retrogradation increases. RS3 formation is highly dependent on amylose content, temperature, prior gelatinization, presence of lipids, proteins and sugars, and source of starch. (Fennema, 1996). High amylose starch was also found to be more resistant to digestion than amylopectin due to its compact linear structure. (Rashmi et al., 2003) A fourth type of RS has been developed by treating starch with chemicals. (Eerlingen, 1994)

Amylose is a linear chain of (1→4)-linked α-D-glucopyranosyl units with some α-D-(1→6) side branches. Alpha-D-(1→6) branches may occur once in every 180-320 units, or in about 0.3-0.5% of the linkages. The molecular weight of amylose is approximately $10^6$ Daltons. Most starches contain about 25% amylose, but some can have up to 70% amylase (e.g., Hi-Maize™ developed by Penford Ingredients; Denver, Colo.). Amylose content is considered the main parameter in starch that determines cooking and eating quality in rice. Amylose content in rice ranges from 18-35% and varies with geographic regions. (TropRice, 2003). Milled rice is classified based on amylose content: waxy (1-2%); non-waxy (>2%); very low (2-9%); intermediate (20-25%); and high (25-33%). Rice grown in Missouri had some 3-18% higher amylose content and a higher proportion of short linear chain amylopectin than the same rice varieties grown in Arkansas or Texas. See A. Aboubacar et al., "The effects of growth location on US rice starch structure and functionality," Whistler Center for Carbohydrate Research and Dept. of Food Science, Purdue University. West Lafayette, Ind. 47907-1160 (2002). RVA (rapid visco amylograph) analysis indicated that rice grown in Missouri had lower peak (1-26%) and breakdown (3-43%) viscosities than both the Arkansas- and Texas-grown rice. Rice varieties with similar amylose content have been reported to have different starch digestibility. See L. N. Panlasigui et al., "Rice varieties with similar amylose content differ in starch digestibility and glycemic response in humans," Am. J. Clin. Nutr., vol. 54, pp. 871-7 (1991).

Amylopectin is a highly branched polymer with a molecular weight from 107 to $5 \times 10^8$, making it one of the largest polymers in nature. Amylopectin is about 75% of most starches. It consists of both (1→4) and (1→6) α-D-glucopyranosyl units. Starches made of 100% amylopectin are called waxy starches, even though there is no wax present. The term "waxy" is used to describe the vitreous or waxy surface when a kernel is cut. Amylopectin is found in the highest proportion in medium, short, and waxy rice, and causes these types of rice to be softer and have a greater tendency to cling. Texture of cooked rice depends on the ratio of amylopectin to amylose.

Digestion of Starch

The hydrolytic enzymes used to digest starches are classified into two types, endo- and exo-enzymes, which digest starch into different end products. For example, amyloglucosidase (glucoamylase), an exo-enzyme, is used commercially to convert starch into glucose. See R. Manelius, "Enzymatic and Acidic Hydrolysis of Native and Modified Starch Granules," Acta Academiae Aboensis, Ser. B., vol. 60(2), pp. 20-21 (2000). Using this enzyme and pre-gelatinized starch, the starch is completely converted to glucose. Glucoamylase cleaves successive α (1,4) and α (1,6)-D-glucosidic linkages from the non-reducing end to produce glucose.

Alpha-Amylase is an endo-enzyme that cleaves α (1,4)-D-glucosidic linkages in starch. The end products after α-amylase digestion of amylopectin are glucose, maltose, maltotriose, and branched α-limit dextins (pentasaccharides). See D. French et al., "The structural analysis and enzymic synthesis of a pentasaccharide alpha-limit dextrin formed from amylopectin by *Bacillus subtilis* alpha-amylase," Carbohydr. Res., vol. 22, pp. 123-134 (1972). On the other hand, pullulanase is a debranching endo-enzyme that cleaves the α (1,6) linkages, especially when separated by at least 2 glucose residues joined by α(1,4) linkages. (Manelius, 2000). Other debranching enzymes, generally termed endo-alpha-1,6-glucanohydrolases, are known such as isoamylase or any other endo-enzyme that exhibits selectivity in cleaving the 1,6-linkages of the starch molecule, leaving the 1,4-linkages substantially intact.

Resistant Starch Formation

Formation of resistant starch type III (RS3) depends on many factors, e.g., pH, temperature, incubation time, storage time, number of heating and cooling cycles, type of starch, and water content. Amylose content and amount of water has been directly correlated to resistant starch yield. See C. Sievert et al., "Enzyme-resistant starch. I. Characterization and evaluation by enzymatic, thermoanalyical and microscropic methods," Cereal Chem., vol. 66, pp. 342-347 (1989).

Resistant starch can be formed through retrogradation. Retrogradation is the precipitation of starch molecules in cooled pastes and gels that contain mainly amylose. The hydrogen bonds within hydrated starch interact, resulting in physical-chemical changes without the creation of permanent chemical bonds. (Berry, 1986). Amylopectin retrogrades very slowly. High amylose starches have a greater retrogradation. Additionally, high amylose starch is more resistant to digestion than amylopectin due to its compact linear structure (Rashmi et al, 2003). Factors that determine rate of retrogradation are the molecular ratio of amylose to amylopectin, the structure of the amylose and amylopectin, temperature, starch concentration, and concentrations of other ingredients, e.g., sugars. See Fennema, 1996; P. L. Russell et al., "Characterization of resistant starch from wheat and maize," J. Cereal Sci., vol. 9, pp. 1-15 (1989); and T. Sasaki et al., "Effect of Amylose Content on Gelatinization, Retrogradation, and Pasting Properties of Starches from Waxy and Nonwaxy Wheat and Their F1 Seeds," Cereal Chem., vol. 77, pp. 58-63 (2000).

When gelatinization occurs in the presence of excess water, resistant starch (RS3) formation is greatly enhanced by retrogradation. Significantly higher levels of RS have been found in cooked pasta than bread. Repeated cycling of autoclaving and cooling, up to 20 cycles, increased RS formation from 20 to over 40%. By raising the autoclave temperature from 121 to 134° C., a decrease in RS yield was seen (Sievert et al, 1989).

Amylose content in starch affects RS yield since RS is retrograded amylose. Amylose will also bind with lipids, proteins and other compounds. The formation of amylose-lipid complexes is reported to compete with and be favored over amylose retrogradation, thus decreasing the RS yield. See R. C. Eerlingen et al., "Enzyme-resistant starch. IV. Effect of endogenous lipids and added sodium dodecyl sulfate on formation of resistant starch," Cereal Chem., vol. 71(2), pp. 170-177 (1994); and L. Slade et al., "Starch and sugars as partially-crystalline water-compatible polymer systems," Cereal Food World, vol. 32(9), p. 680 (1987). Enzymes, such as α-amylase, amyloglucosidase, and pullulanase, have been used to treat waxy and normal maize starches to produce RS after gelatinization. (Berry (1986) Treating amylomaize and amylopectin starches with pullulanase followed by heat yielded higher RS levels than heating alone. Using both heating and pullulanase, RS yields increased in amylomaize and amylopectin starches from 0.3 to 32.4% and from 4.2 to 41.8%, respectively.

Potential Benefits of Resistant Starch

Resistant starch is beneficial in part because as undigestible dietary fiber, it provides bulk to aid in gut peristalsis and thus decrease the transit time of food/waste in the intestine. By consuming 35 g fiber/day, chances of constipation were lower by 60% and heartburn by 30%. Dietary fiber has also been found to help lower cholesterol. See P. Yue et al., "Functionality of resistant starch in food applications," Food Australia, vol. 50, pp. 615ff, as reprinted by National Starch & Chemical Company (1998). Hypercholesterolemic patients that consume up to 50 g dietary fiber/day are benefited by maintaining a normal level of serum cholesterol. Dietary fiber can also lower postprandial serum glucose levels and insulin response by slowing starch digestion. (Fennema, 1996) As a way to increase fiber in the diet, resistant starch can help prevent colon cancer, lower the risk of heart disease, and influence metabolic and inflammatory bowel diseases, such as diabetes and diverticulitis. RS is also a prebiotic because it produces butyrate and other short-chain fatty acids when fermented in the large intestine.

U.S. Pat. No. 4,971,723 discloses a method to produce a partially debranched starch by treating a pre-gelatinized starch with a debranching enzyme, an endo-alpha-1,6-D-glucanohydrolase.

U.S. Pat. No. 5,051,271 discloses a method to produce a food-grade, water insoluble material with water soluble crystalline microparticles by causing the initial starch to undergo retrogradation using a heating and cooling cycle, followed by enzymatic hydrolysis.

U.S. Pat. Nos. 5,281,276 and 5,409,542 disclose a product and a method to increase the yield of resistant starch from a high amylose starch (at least 40%) by initially gelatinizing the starch by heating, followed by incubating the starch with a debranching enzyme for 24 to 48 hours.

U.S. Pat. No. 5,395,640 discloses a method to prepare reduced fat foods by adding a debranched amylopectin starch that is made by gelatinizing the starch, followed by enzymatic debranching.

U.S. Pat. No. 5,480,669 discloses a method to improve the texture of food products with a high fiber content by incorporating resistant starch into the dough, where the resistant starch was made from initially gelatinizing the starch and then debranching enzymatically.

U.S. Pat. Nos. 5,593,503 and 5,902,410 disclose a method to prepare a resistant granular starch from a starch source with at least 40% amylose by heating the starch using a combination of moisture and temperature conditions.

U.S. Pat. No. 5,849,090 discloses a method to make granular resistant starch by heating the starch initially to a temperature from about 60° C. to about 120° C. to swell the starch granules, debranching the swollen starch, and then treating the starch product to retrograde the amylose.

U.S. Pat. No. 5,962,047 discloses a method to produce resistant starch by treating a hydrated starch source, which is optionally debranched, to cause retrogradation, and then to cause enzymatic or chemical hydrolysis.

U.S. Pat. No. 6,043,229 discloses a method to produce resistant starch from a partially degraded starch product (prepared by enzymatic or acid hydrolysis, e.g., potato maltodextrin) using enzymatic debranching with an optional retrogradation step.

U.S. Pat. No. 6,468,355 discloses a method to produce a heat stable starch product with up to 60% resistant starch by partially hydrolyzing the starch with acid, followed by heating the partially hydrolyzed starch.

There is a need for new methods to increase the resistant starch yield from low amylose starches, and to form resistant starch with better cooking properties.

We have discovered a method to produce a resistant starch product that retains the same cooking quality as found in untreated rice starch or flour, but has a higher percentage of starch resistant to α-amylase digestion. This method uses a debranching enzyme, e.g., pullulanase, to digest the starch, but does not require pre-treating the starch source prior to enzymatic treatment. The starch source is neither hydrolyzed nor gelatinized before adding the enzyme. The incubation temperature of the starch and enzyme stays below 60° C. This method produced resistant starch from low amylose starches, rice starch (24%) and rice flour (20%). Surprisingly the resistant starch product formed by this method retained the pasting characteristics of the untreated flour or starch, and was heat stable. The highest yield of resistant starch using this new method was produced from rice starch, up to twelve-fold higher than that found in the native starch. Our best results to date of production of resistant starch with the desired pasting characteristics and heat stability were obtained by incubating the untreated starch with pullulanase at a temperature between about 40° C. and about 60° C., preferably about 55° C., for an incubation period from about 2 hr to about 16 hr, preferably from 2 hr to 4 hr. This method may also be used to produce resistant starch from other botanical sources, e.g., corn, wheat, potato, oat, barley, tapioca, sago, cassaya, and arrowroot. Resistant starch produced by this method has a variety of uses in food products.

PRODUCTION OF RESISTANT STARCH FROM RICE STARCH AND RICE FLOUR

Figure 1:
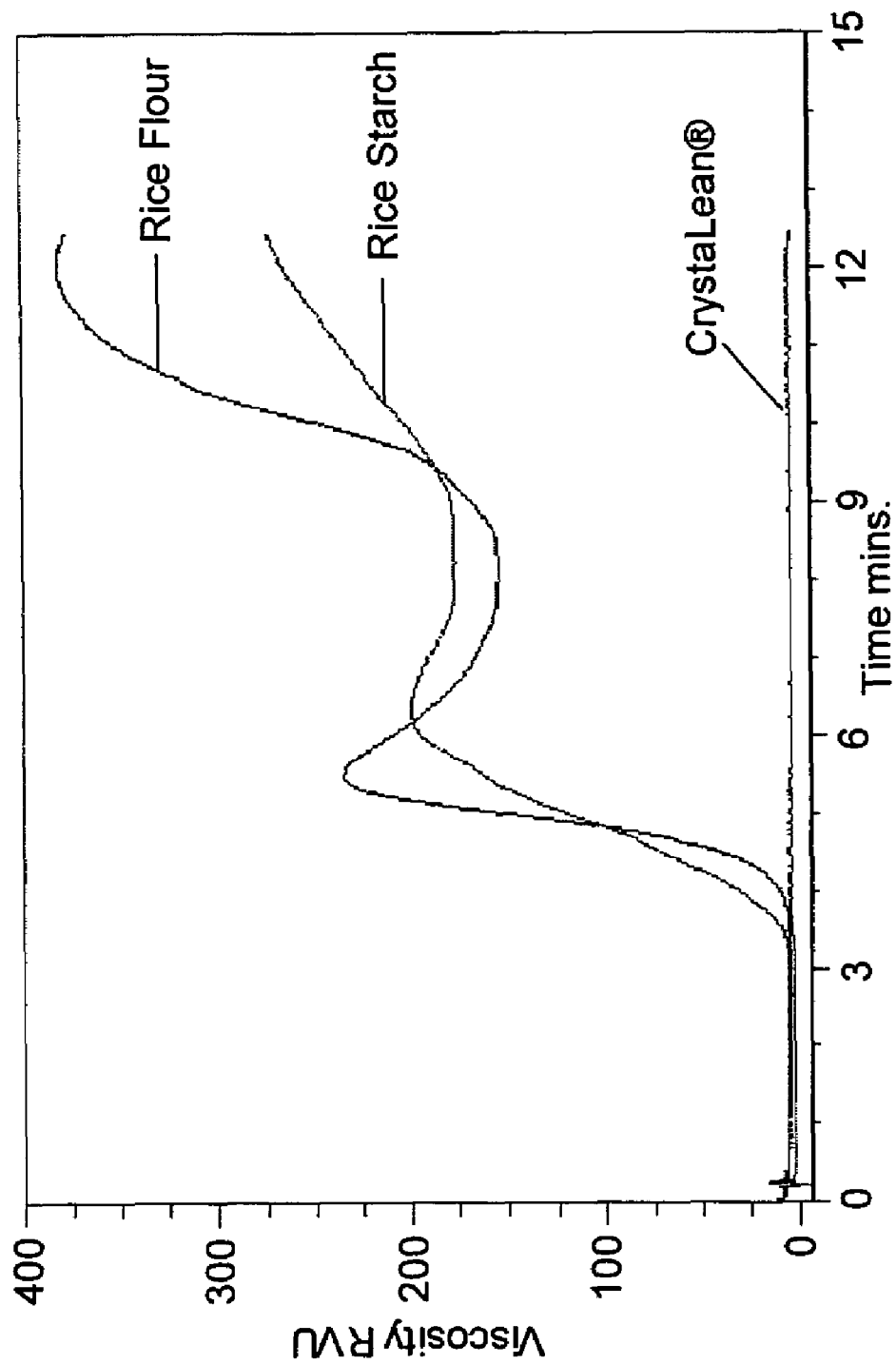
FIG. 1 illustrates the results of rapid visco amylograph analysis, an indication of pasting characteristics, of untreated rice flour, untreated rice starch, and a commercial resistant starch, CrystaLean®.

The starches used in preparing resistant starch of this invention may be derived from any source containing amylose, for example, from corn, potato, barley, sweet potato, wheat, rice, sago, tapioca, cassaya, and sorghum. The method of this invention will work on starches with both high amylose content and low amylose content (less than 30%).

Unlike other methods of producing a product high in resistant starch, the starch is not pre-gelatinized or pre-hydrolyzed prior to treatment with a debranching enzyme. The debranching enzyme, an endo-alpha-1,6-glucanohydrolase, is added to the native starch, and the mixture is then heated to the optimum temperature for the enzyme. For example, if the enzyme pullulanase is used, the mixture is heated to a temperature between about 40° C. to less than 60° C., more preferably about 55° C. Another debranching enzyme may be used, e.g., isoamylase. See U.S. Pat. No. 5,409,542. Optimum concentrations of the enzyme and substrate are governed by the level of enzyme activity, which will vary depending on the enzyme source and concentration. The starch and enzyme incubation in this invention is only about 2 hours to 16 hours, preferably 2 hours to 4 hours, and most preferably about 4 hours. This is in stark contrast to those methods that allow the debranching to continue for 24 to 48 hours. It is believed that the above method can be used to produce a resistant starch product from starch from any source, including wheat, potato, oat, rice, barley, sorghum, corn, arrowroot, cassaya, and sago.

EXAMPLE 1

Methods for Formation of Resistant Rice Starch Using Different Treatments and Enzymes Preparation of Rice Samples Rice flour was obtained from Riviana Foods Inc. (Abbeville, La.) in bulk, while rice starch was purchased from Sigma Chemical Co. (S7260 in kilogram quantities; St. Louis, Mo.). CrystaLean®, a commercially-available resistant starch from corn by Opta Food Ingredients (Bedford, Mass.), was used as a control.

To prepare the samples of starch, one hundred grams of rice starch or rice flour were placed in 2-L Erlenmeyer flasks, and 1400 g of distilled water added. For the "Gelatinized samples" (G), the mixture was stirred and heated on a hot plate to approximately 95° C. The gelatinized samples were divided into two subgroups, one without storage (GNS) and one with 24-hr refrigeration at 3° C. (GS). For the "Non-gelatinized sample" (NG), the mixture was heated only to the recommended temperature for optimal performance of the enzyme to be tested, and enzyme added immediately without any storage time (NGNS). Samples were prepared in duplicate for each treatment.

Enzymatic Treatments and Initial Analyses

Three enzyme-starch incubation periods were tested, 2-, 4-, and 16-hr. Two enzymes were tested, pullulanase (Promozyme™ 400L, Sigma P2986; pullulanase from *Bacillus acidopullulyticus*; minimum 400 units/ml; Sigma Chemical Co.) and α-amylase (Termamyl® 120L, Type L, 120 knu/g; Novo Nordisk Biochem, Franklinton, N.C.). Additionally, a combination of pullulanase-α-amylase was tested. The gelatinized samples were cooled to a temperature that was optimal for each enzyme: 55° C. for pullulanase and 75° C. for α-amylase treatments. For the combination of pullulanase-α-amylase, the sample was cooled to 60° C. The gelatinized/stored samples (GS) were stored overnight in the refrigerator prior to adding enzymes. The NG samples were heated to the optimal temperatures as given above. Ten-ml of each enzyme to be tested was added to each sample; i.e., 10 ml pullulanase to a sample treated only with pullulanase, 10 ml α-amylase to a sample treated only with α-amylase, and both 10 ml pullulanase and 10 ml α-amylase to a sample treated with the combination. After the incubation period, the samples were centrifuged (Model RC-5C from Sorvall Instruments, DuPont) at 8500 rpm for 20 min at 4° C. The residue was collected and frozen at −20° C., then placed in a freeze-dryer sublimator (20 SRC-X; Virtis Co, Inc., Gardiner, N.Y.). After freeze-drying, the sample was weighed, the freeze-dried sample weight (FDSWt). The samples were then milled with a Cyclone Sample Mill (Udy Corporation, Fort Collins, Colo.). Moisture remaining in the samples was measured by weighing samples before and after drying in a Mettler LP16 Infrared Dryer (Mettler-Toledo Incorporation, Hightstown, N.J.).

Resistant Starch Analysis

The total dietary fiber (TDF) content was determined by use of a commercial total dietary fiber kit (Sigma, TDF-100A, St. Louis, Mo.). In the TDF analysis, α-amylase and amyloglucosidase were used to digest any digestible carbohydrate present in the samples. Resistant starch yield was then determined by the glucose oxidase assay as described by B. V. McCleary et al., "Measurement of Resistant Starch. Food Composition and Additives," J. AOAC International, vol. 85, pp. 665-675 (2002). The concentration of resistant starch was determined by digesting the sample with amyloglucosidase to form free glucose, and then detecting the absorbance of free glucose in a spectrophotometer. Resistant starch yield (RS Yield) was calculated based on the weight of enzyme-treated samples (freeze-dried sample weight, FDSWt), taking into consideration the moisture content of the samples. True yield (TY) represented the true resistant starch yield based on the weight of the original untreated rice starch or flour (100 g, including moisture).

In the TDF assay, 200 mg of enzyme-treated, freeze-dried sample was added to a 125 ml Erlenmeyer flask. Ten ml of phosphate buffer, pH 6.0, and α-amylase (0.02 ml) (68,300 units/ml) were added, and the sample mixed. The flask was covered with aluminum foil and placed in a boiling water bath. The sample was then agitated gently at 5-min intervals, and incubated for 15 min after the temperature of the mixture reached 95° C. The solution was then cooled to room temperature, and pH was adjusted to be within the range 4.0-4.6 by adding 0.375 N HCl. After an appropriate pH was obtained, amyloglucosidase (0.02 ml) (10,863 units/ml; Sigma, A 9913) was added. The flask was covered with aluminum foil, placed in a 60° C. agitator-incubator, and incubated for 30 min after the temperature of the sample reached 60° C. Four volumes (10 ml each) 200 proof ethyl alcohol was added to the solution to precipitate the starch, and the flask was left overnight at room temperature to allow complete precipitation. The next day, an additional 10 ml of 200 proof ethyl alcohol, followed by 10 ml of 100% acetone, was added. The sample was then centrifuged 1500 rpm for 5 min, the supernatant discarded, and the residue air dried at room temperature overnight in a hood.

For the glucose oxidase assay, the air-dried sample was analyzed with a purchased kit (Sigma, GAGO-20) that followed the procedure of McCleary et al. (2002). For this assay, 2 ml 2 M potassium hydroxide (KOH) was added to the entire dried sample. After 20 min, 8 ml 1.2 M sodium acetate (pH 3.8) was added, followed by 0.1 ml amyloglucosidase (6,000 units/ml; Sigma, A2986). The sample was vortexed and incubated at 50° C. for 30 min. Then the sample was diluted to a total volume of 100 ml with water and centrifuged at 3000 rpm for 10 min. Resistant starch content was determined by adding 3 ml of glucose oxidase solution with o-dianisidine to a 0.1 ml aliquot of the diluted, centrifuged sample. The mixture was incubated at 50° C. for 20 min, and an absorbance reading at 510 nm was recorded. A blank solution (control reading) was prepared by adding 0.1 ml sodium acetate buffer (0.1 M) to 3 ml glucose oxidase solution with o-dianisidine, and incubating under the same conditions as the rice samples. CrystaLean®, untreated rice starch, and untreated rice flour were also analyzed to use for comparisons. All analyses were conducted in duplicate.

Calculation of Resistant Starch

Calculations of resistant starch followed McCleary et al. (2002:

$$\text{RS Yield (\%)} \atop \text{(samples containing} > 10\% \text{ RS)}: = \Delta E \times F \times (100/0.1) \times$$

$$(1/1000)X(100/W) \times (162/180)$$

$$= \Delta E \times (F/W) \times 90$$

$$\text{RS Yield (\%)} \atop \text{(samples containing} < 10\% \text{ RS)}: = \Delta E \times F \times (10.3/0.1) \times$$

$$(1/1000) \times (100/W) \times (162/180)$$

$$= \Delta E \times (F/W) \times 9.27$$

where, $\Delta E$=absorbance of sample at 510 nm read against a reagent blank

F (conversion from absorbance to micrograms)=100 (μg glucose)/ absorbance of 100 μg glucose W (dry weight of freeze-dried (enzyme-treated) sample)="as is" weight×(100−moisture content)

100/W=starch as a percent of sample weight

162/180=conversion factor, converts free glucose, as determined, to anhydroglucose as occurs in starch 10.3/0.1=volume correction (0.1 mL taken from 10.3 mL) for samples containing 0-10% RS where the incubation solution was not diluted, and the final volume is 10.3 mL (McCleary et al., 2002).

True Yield based on dry weight of 100 g untreated flour or starch=[RS %×freeze-dried weight of enzyme-treated sample]/(dry weight of untreated flour or starch)

Example of resistant starch calculation using the sample from NGNS2 hr-pullananse-treated rice starch:

$$F = 100 / [(1.348 + 1.382 + 1.322)/3]$$

$$= 74.07 \text{ (based on 3 replicates of the}$$

$$100 \mu g/ml \text{ glucose standard solutions)}$$

$$W = 100\% - 6.97\%$$

$$= 93.03\%$$

$$\text{RS Yield} = 0.533 \times [74.07/(93.03)] \times 90$$

$$= 38.19\%$$

Dry weight of 100 g of untreated rice starch=86.94 g
True Yield (based on dry weight of untreated rice starch)= (38.19%×67.91 g)/86.94 g=29.83%

Statistical Analysis

SAS (Statistical Analysis System) software (version 8.0) was used. Post-hoc multiple comparisons were performed using Tukey's studentized range test to test the interactions of incubation period and gelatinization type in enzyme-treated rice flour and starch. The effects of the treatments on RS yield (RSY), true yield (TY), and freeze-dried sample weight (FD-SWt) were examined. The level of significance used was $p \leq 0.05$. Abbreviations used in the following tables and graphs for the various samples are: GS for gelatinization with storage, NGNS for no gelatinization and no storage, and GNS for gelatinization and no storage; rice flour (RF) or starch (RS).

Proximate Analysis

Rice starch and rice flour were analyzed for fat, carbohydrate, protein, and ash content as described in H. J. An, "Properties of Ohmically Heated Rice Starch and Rice Flour," Doctorate Thesis, Department of Food Science, Louisiana State University, Baton Rouge, Louisiana (2001). Sample moisture was measured as described above, and the results are given in Table 1. All samples were measured in duplicate. As seen in Table 1, the major differences between rice starch and rice flour were the increased amount of fat and protein in rice flour.

TABLE 1

Proximate analysis of Rice Starch and Rice Flour (% wet basis)

| Sample | Composition (%) | | | | | |
|---|---|---|---|---|---|---|
| | Carbohydrate | Fat | Protein | Moisture | Ash | Amylose |
| Commercial Rice Starch | 86.06 | 0.01 | 0.56 | 13.06 | 0.31 | 23.6 |
| White Rice Flour | 78.79 | 0.71 | 7.77 | 12.05 | 0.59 | 19.4 |

EXAMPLE 2

Effect of Pullulanase Treatment on Rice Flour

The results of the treatment and analysis discussed in Example 1 for use of the enzyme pullulanase on rice flour are shown in Table 2. The RS content of the commercial control, CrystaLean®, was 57.8% (RS Yield, RSY), and 65.7% based on dry weight of untreated CrystaLean® (True Yield, TY). RSY for the untreated rice flour was 1.32%, and TY was 1.50%. The RSY and TY for non-gelatinized rice four treated with pullulanase (NGNS2 hr (4.57% RSY, 4.21% TY), NGNS4 hr (4.48% RSY, 4.10% TY), and NGNS16 hr (3.57% RSY, 3.25% TY)) were not significantly different (Table 2). However, both RSY and TY were significantly different from the commercial control and untreated rice flour (p<0.05). Two of the gelatinized, no storage rice samples, GNS2 hr and GNS4 hr, had 0.95% and 1.24% TY, respectively, and were not significantly different from the untreated rice flour. The other gelatinized samples, (GNS16 hr, 9.71% TY; GS2 hr, 12.7% TY; GS4 hr, 10.6% TY, GS16 hr, 16.8% TY) were significantly different from the commercial control and untreated rice flour (p<0.05). These TY values were approximately one-sixth of the commercial control, and 6 to 8 times that of the untreated rice flour (Table 2). GS16 hr produced both the highest RSY and TY values, 17.3% and 16.8%, respectively.

TABLE 2

Effects of Gelatinization/Storage and Incubation Duration on Pullulanase Treatments on Rice Flour RS Formation

| Sample | Treatment | RSYield[1] (%) | True Yield[2] (%) | Moisture (%) | FDSWt[3] (g) |
|---|---|---|---|---|---|
| Commercial Control | — | 57.8a[4] | 65.7a | 10 | 100a |
| Rice Flour | — | 1.32f | 1.50d | 12.05 | 100a |
| Pullanase | NGNS2hr | 4.57e | 4.21d | 7.00 | 81.0bc |
| | NGNS4hr | 4.48e | 4.10d | 5.97 | 80.5bc |
| | NGNS16hr | 3.57e | 3.25d | 5.79 | 80.0bc |
| | GNS2hr | 8.67d | 0.95d | 6.79 | 11.5e |
| | GNS4hr | 8.67d | 1.24d | 9.43 | 12.2e |
| | GNS16hr | 13.6c | 9.71c | 7.50 | 63.0d |
| | GS2hr | 13.0c | 12.75c | 9.47 | 84.0b |
| | GS4hr | 12.8c | 10.6c | 5.99 | 73.2c |
| | GS16hr | 17.3b | 16.8b | 11.2 | 85.2b |

[1]RSYield = Resistant starch yield in percent;
[2]True Yield = [RSYield × (freeze-dried weight of enzyme treated rice starch)]/(dry weight of untreated rice flour);
[3]FDSWt = Sample weight after enzyme treatment followed by freeze-drying;
[4]Means with different letters within each column are significantly different at p ≦ 0.05. The values are an average of 4 measures.

Overall comparison indicated that longer incubation with pullulanase produced higher TY values, e.g., TY at GS16 hr and GNS16 hr as compared to the 2 hr and 4 hr values. GNS16 hr had a similar TY to GS2 hr and GS4 hr, indicating that overnight storage prior to enzyme treatments could substantially increase RS formation from rice flour.

Non-gelatinized (NGNS) treatments produced TY (3-4%) that were four times higher than that of GNS2 hr and GNS4 hr (1%) (Table 2). The gelatinized (GS) samples were 3 to 5 times higher in TY than the NGNS samples.

EXAMPLE 3

Effects of α-Amylase Treatment on Rice Flour

For rice flour treated with α-amylase as described in Example 1, the results are shown in Table 3. The lowest TY was 0.45% from NGNS4 hr and GNS16 hr (Table 3). GS2 hr produced the highest TY at 2.28%. All samples except GS2 hr were similar to the untreated rice flour and each other in TY. The TY of all samples was significantly ($p \leq 0.05$) lower than the commercial control.

TABLE 3

Effects of Gelatinization/Storage and Incubation Duration on α-Amylase Treatment on Rice Flour RS Formation

| Sample | Treatment | RSYield[1] (%) | True Yield[2] (%) | Moisture (%) | FDSWt[3] (g) |
|---|---|---|---|---|---|
| Commercial Control | — | 57.8a[4] | 65.7a | 10 | 100a |
| Rice Flour | — | 1.32f | 1.50bc | 12.05 | 100a |
| α-Amylase | NGNS2hr | 4.41e | 1.26bc | 9.48 | 22.5bc |
| | NGNS4hr | 4.16e | 0.45c | 8.03 | 9.40d |
| | NGNS16hr | 3.46e | 0.98c | 8.98 | 23.0b |
| | GNS2hr | 6.90cd | 0.82c | 8.47 | 10.5cd |
| | GNS4hr | 7.03cd | 0.75c | 8.54 | 9.35d |
| | GNS16hr | 5.23de | 0.45c | 8.56 | 7.6d |
| | GS2hr | 11.6b | 2.28b | 5.49 | 17.3bcd |

TABLE 3-continued

Effects of Gelatinization/Storage and Incubation Duration on α-Amylase Treatment on Rice Flour RS Formation

| Sample | Treatment | RSYield[1] (%) | True Yield[2] (%) | Moisture (%) | FDSWt[3] (g) |
|---|---|---|---|---|---|
| | GS4hr | 10.56b | 1.17bc | 7.48 | 9.80d |
| | GS16hr | 7.23c | 1.06c | 7.52 | 13.0bcd |

[1]RSYield = Resistant starch yield in percent calculated (McCleary, 2002)
[2]True Yield = [RS Yield × (freeze-dried weight of enzyme treated rice starch)]/(dry weight of untreated rice flour)
[3]FDSWt = Sample weight after enzyme treatment followed by freeze-drying
[4]Means with different letters within each column are significantly different at p ≦ 0.05. The values are an average of 4 measures.

GS2 hr had the highest RSY at 11.64% (Table 3), but was not significantly different than GS4 hr. However, this RSY was one-fifth of the commercial control. GS16 hr was similar to GNS2 hr and GNS4 hr in RSY, and was 2% higher than GNS16 hr. Within the GS treatments, longer incubation time decreased RSY as GS16 hr had 7.23% RSY, while GS2 hr and GS4 hr had approximately 10%. The non-gelatinized (NGNS) treatments had similar RSY and TY values over the time periods. However, NGNS4 hr had only 9.4 g FDSWt, which was half of NGNS2 hr and NGNS16 hr, 22.5 g and 23 g, respectively. The incubation temperature for α-amylase treatments was 75° C., which is above the gelatinization temperature of rice flour. This temperature may have facilitated hydrolysis of starch molecules into glucose, maltose and α-dextrins, resulting in the low yields.

EXAMPLE 4

Effects of α-Amylase-Pullulanase Treatment on Rice Flour

For the treatment of rice flour with the enzyme combination of α-amylase-pullulanase as described in Example 1, the results are shown in Table 4. GS16 hr produced the lowest TY, 0.3%, while NGNS2 hr and NGNS4 hr produced the highest TY at 2.6% (Table 4). NGNS16 hr, GNS (2, 4, 16 hr), and GS (4, 16 hr) were not different in TY, <1%. TY values for GS2 hr and GS4 hr were similar to the untreated rice flour at 1.5%.

TABLE 4

Effects of Gelatinization/Storage and Incubation Duration on α-Amylase-Pullulanase Treatment on Rice Flour RS Formation

| Sample | Treatment | RSYield[1] (%) | True Yield[2] (%) | Moisture (%) | FDSWt[3] (g) |
|---|---|---|---|---|---|
| Commercial Control | — | 57.77a[4] | 65.69a | 10 | 100a |
| Rice Flour | — | 1.32e | 1.50c | 12.1 | 100a |
| αAmylase-Pullulanase | NGNS2hr | 3.69d | 2.64b | 5.96 | 63b |
| | NGNS4hr | 4.32d | 2.62b | 6.50 | 53.5c |
| | NGNS16hr | 3.16d | 0.32e | 7.50 | 9f |
| | GNS2hr | 5.91c | 0.61de | 6.53 | 9.225f |
| | GNS4hr | 5.97c | 0.57e | 7.52 | 8.5f |
| | GNS16hr | 6.10c | 0.58e | 7.02 | 8.465f |
| | GS2hr | 7.80b | 1.49cd | 6.24 | 16.8d |
| | GS4hr | 7.44b | 0.96cde | 7.30 | 11.45e |
| | GS16hr | 5.84c | 0.30e | 7.19 | 4.65g |

[1]RSYield = Resistant starch yield in percent calculated (McCleary, 2002)
[2]True Yield = [RS Yield × (freeze-dried weight of enzyme treated rice starch)]/(dry weight of untreated rice flour)
[3]FDSWt = Sample weight after enzyme treatment followed by freeze-drying
[4]Means with different letters within each column are significantly different at p ≦ 0.05. The values are an average of 4 measures.

RSYield % increased significantly (p≦0.05) with all enzyme treatments over untreated rice flour. However, the TY value only increased slightly for two treatments (NGNS2 hr and NGNS4 hr). Gelatinization did not cause a significant increase (p≧0.05) in TY; however, the FDSWt was significantly higher (p≦0.05) in the NGNS2 hr and 4 hr samples.

EXAMPLE 5

Effect of Pullulanase Treatment on Rice Starch

The results of pullulanase treatment of rice starch (as described in Example 1) are given in Table 5. RSY and TY of untreated rice starch were about 10% of the commercial control (Table 5). The lowest RSY for treated samples was 12.6% for GNS2 hr, and the highest was NGNS4 hr at 71.5%. These percentages translated to TY values of 3.32% and 61.1%, respectively. For non-gelatinized samples, NGNS4 hr was not significantly different from the commercial control. NGNS2 hr and NGNS16 hr were not significantly different from the commercial control, but were significantly lower than NGNS4 hr in RSY (p≦0.05). For gelatinized samples, GNS2 hr was significantly lower than GNS16 hr in RSY (p≦0.05). GNS16 hr had slightly more than double the RSY of GNS2 hr, and the TY for GNS16 hr was approximately 6 times more than GNS2 hr.

TABLE 5

Effects of Gelatinization/Storage and Incubation Duration on Pullulanase Treatments on Rice Starch RS Formation

| Sample | Treatment | RSYield[1] (%) | True Yield[2] (%) | Moisture (%) | FDSWt[3] (g) |
|---|---|---|---|---|---|
| Commercial Control | — | 57.8ab[4] | 57.8ab | 10.0 | 100a |
| Rice Starch | — | 5.39e | 5.39ef | 13.06 | 100a |
| Pullulanase | NGNS2hr | 48.7b | 41.0c | 6.48 | 77.0b |
| | NGNS4hr | 71.5a | 61.1a | 7.01 | 80.0b |
| | NGNS16hr | 48.9b | 43.3bc | 6.51 | 82.5b |
| | GNS2hr | 12.6de | 3.32f | 5.98 | 25.0d |
| | GNS4hr | 14.7cde | 3.85f | 5.61 | 24.2d |
| | GNS16hr | 29.6c | 18.1de | 4.73 | 56.2c |
| | GS2hr | 19.3cde | 16.1edf | 7.03 | 78.3b |
| | GS4hr | 20.7cde | 15.6edf | 4.67 | 69.1bc |
| | GS16hr | 26.8cd | 22.4d | 7.71 | 78.8b |

[1]RSYield = Resistant starch yield in percent calculated (McCleary, 2002)
[2]True Yield = [RS Yield × (freeze-dried weight of enzyme treated rice starch)]/(dry weight of untreated rice flour)
[3]FDSWt = Sample weight after enzyme treatment followed by freeze-drying
[4]Means with different letters within each column are significantly different at p ≦ 0.05. The values are an average of 4 measures.

The gelatinized (GS) treatments were not significantly different (p>0.05) from each other. As the incubation time increased, the RSY and TY increased slightly, with a range of 20-26% RSY and 15-22% TY. All NGNS and 16 hr treatments resulted in significantly greater RS content than the untreated rice starch control (p≦0.05), except for GNS16 hr. The non-gelatinized samples (NGNS) had higher TY values than any other treatment, values close to the commercial control. The high TY values in the NG samples may reflect that the starch granules were more intact than in the gelatinized samples.

The GNS samples had the lowest FDSWt (24.2 to 56.2 g). The GS rice starch had significantly higher FDSWt (p≦0.05) than the GNS samples. This was likely due to the overnight refrigeration in the GS samples which allowed the gelatinized starch to retrograde and become more resistant to enzyme digestion.

EXAMPLE 6

Effects of α-Amylase Treatment on Rice Starch

For α-amylase treatment on rice starch, the results are shown Table 6. NGNS2 hr and NGNS4 hr were not significantly different from each other in RSYield. GS4 hr had the highest RSY at 70.8%, however the TY was only 3.4% due to a low FDSWt, 4.54 g. NGNS2 hr and NGNS4 hr had similar RSY to the untreated rice starch. The GNS treatments had the lowest TY, 0.22%, lower than the untreated rice starch. NGNS16 hr had the highest TY at 14.5%.

The effects of gelling the samples prior to enzyme treatment were significant (p≦0.05). The NGNS treatment yielded significantly higher FDSWt (25 to 70 g) and TY (3.18 to 14.5%). The GNS samples had about 1 g of sample left after freeze-drying with 0.2% TY, while GS had 3.32 to 8.60 g and 2.24 to 4.37% TY. Gelatinization of rice starch prior to enzyme treatment made the starch granules more accessible to enzyme digestion.

TABLE 6

Effects of Gelatinization/Storage and Incubation Duration on α-Amylase Treatments on Rice Starch RS Formation

| Sample | Treatment | RSYield[1] (%) | True Yield[2] (%) | Moisture (%) | FDSWt[3] (g) |
|---|---|---|---|---|---|
| Commercial Control | — | 57.8b[4] | 57.8a | 10.0 | 100a |
| Rice Starch | — | 5.39e | 5.39c | 13.06 | 100a |
| α-Amylase | NGNS2hr | 7.53e | 5.61c | 7.68 | 70.0b |
| | NGNS4hr | 5.03e | 3.18de | 9.04 | 60.5c |
| | NGNS16hr | 56.1bc | 14.5b | 9.89 | 25.0d |
| | GNS2hr | 24.5d | 0.27f | 6.61 | 1.05h |
| | GNS4hr | 25.2d | 0.22f | 5.1 | 0.81h |
| | GNS16hr | 25.0d | 0.25f | 5.75 | 0.94h |
| | GS2hr | 48.5c | 4.37cd | 8.00 | 8.60e |
| | GS4hr | 70.8a | 3.41de | 7.75 | 4.54f |
| | GS16hr | 67.1a | 2.24e | 12.3 | 3.32g |

[1]RSYield = Resistant starch yield in percent calculated (McCleary, 2002)
[2]True Yield = [RSYield × (freeze-dried weight of enzyme treated rice starch)]/(dry weight of untreated rice flour)
[3]FDSWt = Sample weight after enzyme treatment followed by freeze-drying
[4]Means with different letters within each column are significantly different at p ≦ 0.05. The values are an average of 4 measures.

The FDSWt values were higher in the GNS and GS samples for rice flour than rice starch (Tables 3 and 6), but not in the NGNS rice flour. This could reflect the presence of higher amounts of amylose-lipid complexes in rice flour due to its higher fat content (Table 1). The lower FDSWt in NGNS rice flour may be a result of α-amylase digesting the amylose-lipid complexes present. Table 1 indicates that amylose content in rice starch (23.6%) was significantly higher than in rice flour (19.4%) (p≦0.05). Tables 3 and 6 also indicate that untreated rice starch had a higher amount of resistant starch than rice flour.

EXAMPLE 7

Effect of α-Amylase-Pullulanase Treatment on Rice Starch

The results of treating rice starch with the combination of α-amylase and pullulanase (as described in Example 1) is given in Table 7. Based on RSY, NGNS16 hr had the lowest yield at 12.51%, while GS16 hr had the highest yield at 52.3%. However, both treatments produced very low TY. NGNS16 hr, GNS2 hr, GNS4 hr, GNS16 hr and GS16 hr had less than 2 g (freeze-dried sample weight) remaining after enzyme treatment. Therefore even though GS16 hr had 52.28% RSY, it had only 1.16% TY. NGNS16 hr had only 0.19% TY. After factoring in the FDSWt, NGNS4 hr had the highest TY at 22.9% (Table 7). NGNS16 hr, GNS (2, 4, 16 hr), and GS (4, 16 hr) were significantly lower than the commercial control, untreated rice starch, and other treatments in TY ($p \leq 0.05$). With this enzyme combination, longer incubation time resulted in lower TY and FDSWt.

TABLE 7

Effects of Gelatinization/Storage and Incubation Duration on
α-Amylase-Pullulanase Treatments on Rice Starch RS Formation

| Sample | Treatment | RSYield[1] (%) | True Yield[2] (%) | Moisture (%) | FDSWt[3] (g) |
|---|---|---|---|---|---|
| Commercial Control | — | 57.8a[4] | 57.8a | 10.0 | 100a |
| Rice Starch | — | 5.39h | 5.39c | 13.06 | 100a |
| α-Amylase-Pullulanase | NGNS2hr | 37.3bcde | 20.5b | 8.03 | 52.0b |
| | NGNS4hr | 49.7abc | 22.8b | 7.02 | 43.0c |
| | NGNS16hr | 12.5gh | 0.19d | 7.52 | 1.45f |
| | GNS2hr | 21.6fg | 0.41d | 4.80 | 1.75f |
| | GNS4hr | 23.2efg | 0.35d | 3.83 | 1.40f |
| | GNS16hr | 36.6cdef | 0.60d | 4.32 | 1.48f |
| | GS2hr | 41.9bcd | 5.19c | 6.53 | 11.9d |
| | GS4hr | 30.8def | 1.87d | 6.45 | 6.25e |
| | GS16hr | 52.3ab | 1.16d | 6.49 | 1.81f |

[1]RSYield = Resistant starch yield in percent calculated (McCleary, 2002)
[2]True Yield = [RSYield × (freeze-dried weight of enzyme treated rice starch)]/(dry weight of untreated rice flour)
[3]FDSWt = Sample weight after enzyme treatment followed by freeze-drying
[4]Means with different letters within each column are significantly different at $p \leq 0.05$. The values are an average of 4 measures.

The gelatinized samples, GS and GNS, had significantly lower FDSWt than the NGNS samples, except for NGNS16 hr ($p \leq 0.05$). The NGNS samples were approximately 40 to 50 g higher in FDSWt, and 15 to 20% higher in TY. The GS2 hr sample had the highest TY (5.19%) and FDSWt (11.9 g) among the GS and GNS samples; however it was not significantly different from the untreated rice starch in TY.

Pullulanase is a debranching enzyme and produces oligosaccharides from starch molecules, while α-amylase is an endo-enzyme that cleaves α (1,4) linkages randomly to produce glucose, maltose, maltotriose and branched α-limit dextins. Among the three enzyme treatments for both rice flour and starch, pullulanase alone produced the least breakdown in the starch. This was visually evident after the enzyme treatments. The liquid present in the pullulanase treatment flasks was clear and odorless, while the α-amylase and α-amylase-pullulanase treatments had brown and sweet smelling liquid. The starch molecules present were digested by α-amylase to produce simple sugars, thus explaining the lower yield than with pullulanase alone. The α-amylase-pullulanase combination similarly produced lower yields, especially in the gelatinized samples.

Without wishing to be bound by this theory, it is believed that pullulanase debranched the starch molecules, making the starch molecules even more accessible to α-amylase digestion. Gelatinization of the rice flour and starch resulted in disrupted starch granules making starch molecules more accessible to enzymes. When gelatinization was combined with the synergistic effects of α-amylase and pullulanase, most of the starch was digested, leaving little resistant starch. In the pullulanase treatments, the debranching enzyme cleaved the amylopectin branches to create linear amylose chains. These chains were allowed to realign and crystallize into resistant starch since α-amylase was not present to further degrade the linear chains. Pullulanase was unable to further degrade the linear chains since it only cleaves α (1,6) linkages. Therefore pullulanase yielded the highest amount of resistant starch among the three enzyme treatments.

These results indicate that the choice of enzymes and pretreatment of starch could affect RS formation. Pullulanase at 4 hr produced the highest amount of RS among the three enzyme combinations, followed by α-amylase-pullulanase, and then α-amylase. Rice starch had higher RS formation than rice flour, especially in the pullulanase-treated samples. Non-gelatinized (NGNS) treatments of rice starch had 40-60% of TY, while NGNS treatments of rice flour had only 4% TY. The highest TY in rice flour was in the GS pullulanase treatments, a range of 10-17%. Within the pullulanase treatments, the longer incubation treatments produced higher TY.

Pasting Characteristics of Resistant Rice Prepared from Rice Flour and Starch Using Different Enzyme Treatments When starch is heated past gelatinization in excess water so that the starch granules swell and become totally disrupted, a viscous mass (paste) is formed. This process is called pasting. The rapid visco amylograph (RVA) measures the pasting characteristics of starch in rapid visco units (RVU). The pasting temperature (PT) is the temperature at which viscosity of a sample begins to increase. A lower PT indicates faster swelling. The peak viscosity (PV) measures the extent of swelling. During cooking, the starch paste becomes usable once the starch is heated past PV. The time to peak (TP) is the time required to cook the starch to reach PV. The breakdown (BKD) viscosity is the drop in viscosity from the maximum value (PV) to the minimum value (MV). BKD indicates the stability of the starch paste during cooking, and the cooked paste stability is indicated by final viscosity (FV) at 50° C. The total setback (TSB) is the viscosity increase as the paste is cooled to 50° C. TSB is an indicator of extent of retrogradation of starch. These values were measured by RVA and compared for the resistant rice starch samples formed in Example 1 from rice flour and rice starch.

EXAMPLE 8

Materials and Methods for Pasting Experiments
Rapid Visco Amylograph Analysis

Freeze-dried samples of resistant rice starch from Example 1 were analyzed by a rapid visco amylograph (RVA) (Newport Scientific, Foss Food Technology, Eden Prairie, Minn.). Apparent viscosity of samples was measured in units of RVU (rapid viscosity units), and recorded as a function of both temperature and time. Procedures for sample preparation were as directed by the RVA manufacturer. The amount of sample and water to be used in the RVA analysis was calculated using the following formulas:

$$S = (88*3.0)/100 - M$$

$$W = 25 + (3.0 - S)$$

Where, S=corrected sample mass (g)
W=corrected water volume (mL)
M=actual moisture content of the sample (%)

The sample mass and calculated water volume were added to a RVA canister, and the canister lowered into the RVA. From 0 to 10 sec in the RVA, the temperature was 50° C., and spindle speed was 960 rpm. From 10 sec to 1 min, the spindle speed decreased to 160 rpm, but temperature remained at 50° C. The spindle speed remained at 160 rpm for the remainder of the test. From 1 min to 4:48 min, the temperature increased linearly from 50 to 95° C. From 4:48 min to 7:18 min, the temperature was held at 95° C. From 7:18 min to 11:06 min, the temperature decreased linearly from 95 to 50° C. The temperature remained at 50° C. from 11:06 min to 12:30 min, when the test ended. Readings were taken every 4 sec. The idle temperature of the RVA was 50±1° C. Each sample was analyzed twice using RVA. Peak viscosity (PV), minimum viscosity (MV), final viscosity (FV), pasting temperature (PT), and time to peak viscosity (TP) were recorded. Set back (SBK), total set back (TSB), and breakdown (BKD) were computed by the following formulas: SBK=FV−PV; TSB=FV−MV; and BKD=PV−MV. All measurements were reported in rapid visco units (RVU).

Statistical Analysis and Sample Abbreviations

SAS (Statistical Analysis System) software (version 8.0) was used. Post-hoc multiple comparisons were performed using Tukey's studentized range test to study the interaction of incubation time and gelatinization in each enzyme treatment on rice starch and rice flour. The enzyme treatments were α-amylase (T), pullulanase (P), α-amylase-pullulanase (PT). Incubation periods were 2, 4, 16 hours. Abbreviations were GS for gelatinization with storage, NGNS for no gelatinization without storage, GNS for gelatinization without storage; rice flour (RF) and starch (RS). The level of significance was $p \leq 0.05$.

EXAMPLE 9

Effect of Pullulanase on Pasting Characteristics of Rice Flour

Figure 2:
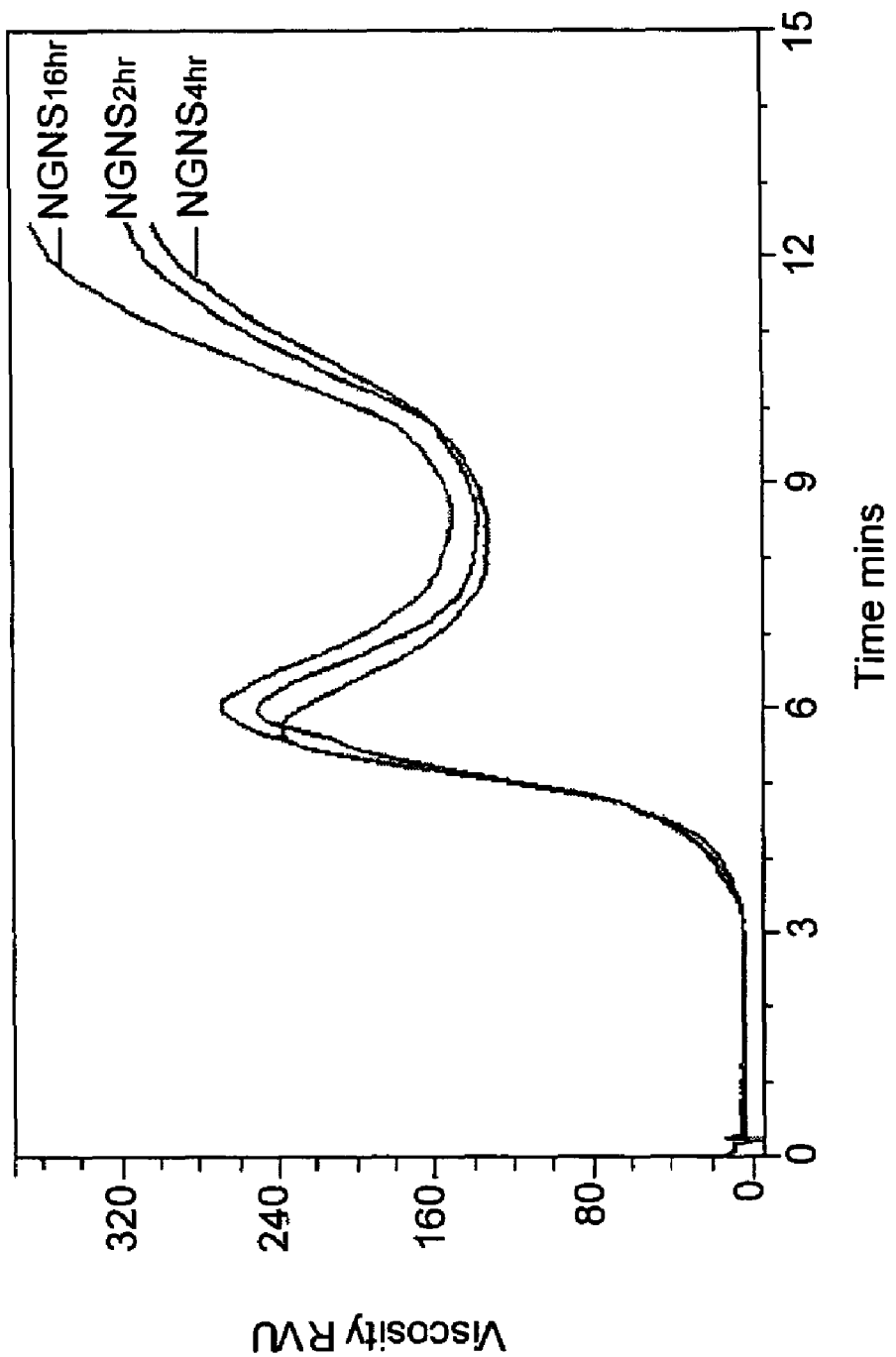
FIG. 2 illustrates the results of rapid visco amylograph analysis of non-gelatinized rice flour that was not stored before being incubated with the enzyme pullulanase for either 2 hr (NGNS2 hr), 4 hr (NGNS4 hr), or 16 hr (NGNS16 hr).

For the pullulanase treated samples, all NGNS (2, 4, 16 hr) treatments were significantly different ($p \leq 0.05$) from the commercial control in PV, MV, BKD, FV, SBK, TSB and TP (Table 8, FIGS. 1 and 2). As in Example 1, the control was a commercial resistant starch, CrystaLean®. In making CrystaLean®, the corn starch had been preheated, and therefore indicated no pasting characteristics in RVA. The CrystaLean® control had 5.75 RVU (PV), 4.42 RVU (MV), and 4.92 RVU (FV). The NGNS samples were treated with pullulanase at 55° C. The gelatinization temperature of rice flour is between 70-92° C.; therefore during the pullulanase enzyme treatment, the NGNS-treated samples did not undergo gelatinization. The gelatinized (GNS and GS) samples (FIGS. 3 and 4) had been cooked before enzyme-incubation. They were significantly lower in viscosity ($p \leq 0.05$) than the NGNS-treated samples and the untreated rice flour. The GNS and GS-treated samples did not have any pasting qualities after their enzyme treatments.

NGNS (2, 4, 16 hr) were not significantly different in PV and MV from the untreated rice flour. NGNS2 hr had similar breakdown value as the untreated rice flour (Table 8). NGNS16 hr had the highest breakdown (BKD) among the NGNS treatments, 50 RVU higher than untreated rice flour (Table 8). The greater the BKD, the less stable the starch is during cooking. Thus, NGNS16 hr had the lowest cooking stability. It was likely that the 4 hr and 16 hr incubations had debranched more starch molecules and reduced their stability in heat. However upon cooling, the FV for NGNS2 hr and NGNS4 hr increased by 100 and 56 RVU, respectively, and exceeded their PV. NGNS16 hr had a FV that was almost identical to its PV, 233 RVU (Table 8). There was no difference ($p > 0.05$) in SBK, TSB, FV, and TP between the NGNS samples and the untreated rice flour. The TSB values suggested that the NGNS samples had less potential for retrogradation than untreated rice flour. The TSB for NGNS ranged from 40-90 RVU lower than the untreated rice flour.

Figure 3:
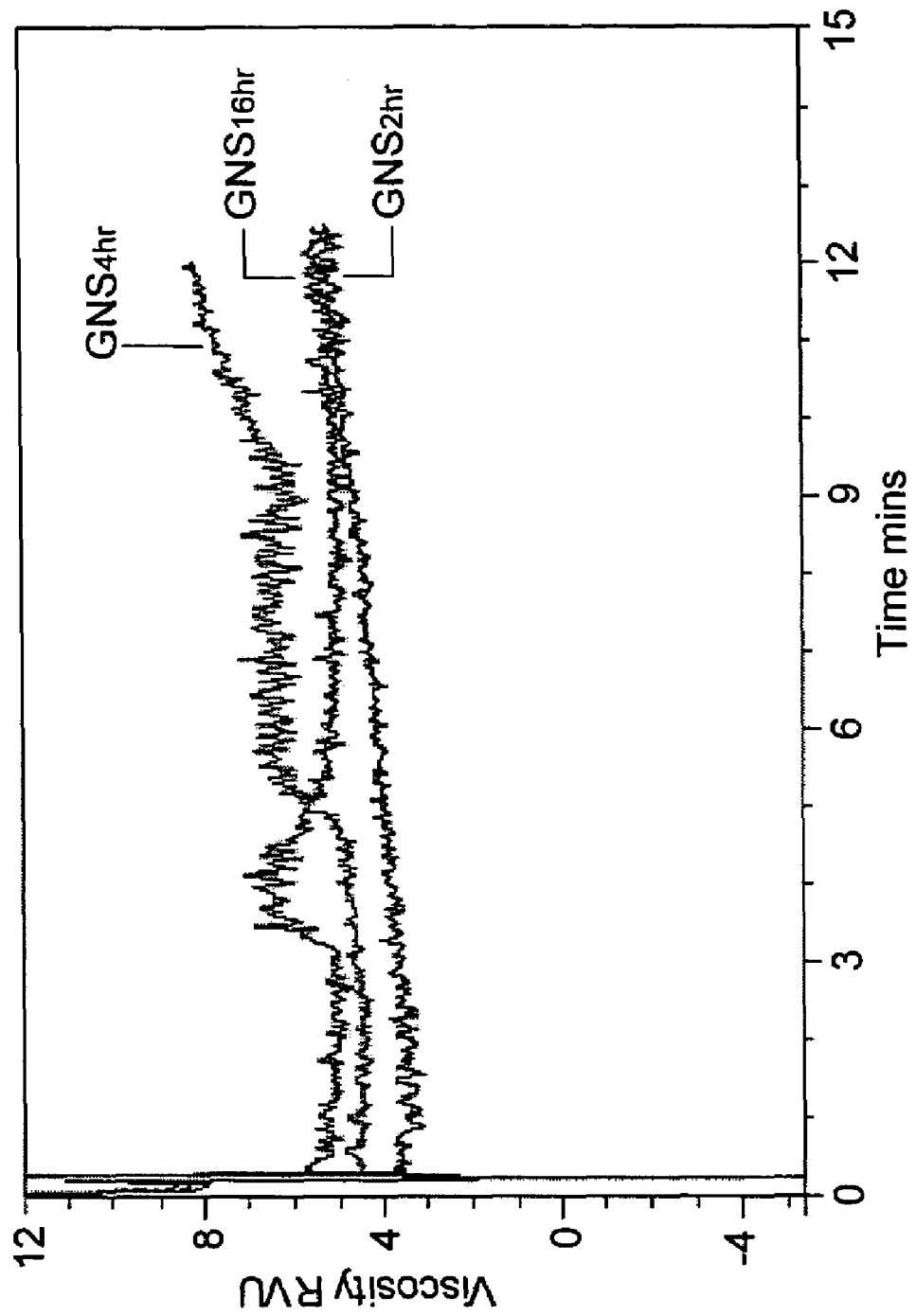
FIG. 3 illustrates the results of rapid visco amylograph analysis of gelatinized rice flour that was not stored before being incubated with pullulanase for either 2 hr (GNS2 hr), 4 hr (GNS4 hr), or 16 hr (GNS16 hr).
Figure 4:
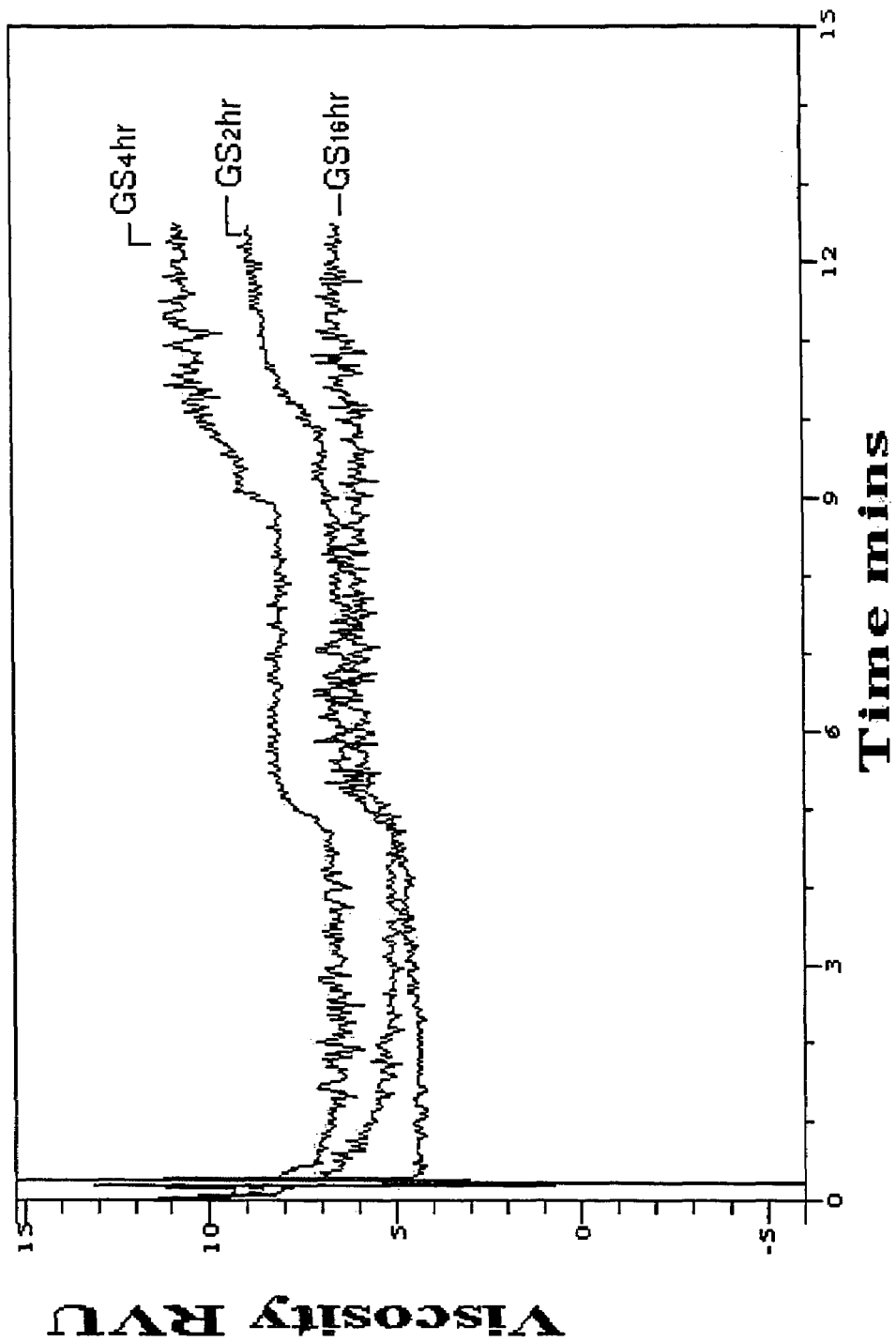
FIG. 4 illustrates the results of rapid visco amylograph analysis of gelatinized rice flour that was stored overnight before being incubated with pullulanase for either 2 hr (GS2 hr), 4 hr (GS4 hr), or 16 hr (GS16 hr).

The GNS and GS samples had no significant difference from the commercial control in all pasting parameters except TP (Table 8, FIGS. 1, 3, and 4). No pasting was observed in these samples or in the commercial control. These samples had been gelatinized prior to enzyme treatment by cooking at 95° C. The BKD, SBK and TSB values were low as little to no increase in viscosity occurred during the RVA test.

The PT for NGNS4 hr and NGNS16 hr was at 83.6° C., while the PT for untreated rice flour and NGNS2 hr was 86° C. The NGNS samples took slightly less than 6 min to cook, just like untreated rice flour. The GNS and GS samples were reported to cook at 3.7 to 6.3 min. However, when referring to the RVA thermograms, neither a pasting peak nor a PT was found (Table 8).

The incubation time did not significantly affect the pasting characteristics of any sample (Table 8). On the other hand, gelatinization type had an effect on the pasting characteristics.

TABLE 8

Effects of Gelatinization/Storage and Incubation Duration on Pasting Characteristics of Pullulanase Treated Rice Flour[1,2,3]

| Sample | Treatment | PV | MV | BKD | FV | SBK | TSB | TP | PT |
|---|---|---|---|---|---|---|---|---|---|
| Control | — | 5.75b[3] | 4.42b | ND | 4.92b | ND | ND | 2.2811d | ND |
| Rice Flour | — | 235.83a | 154.63a | 81.21c | 377.21a | 141a | 222.58a | 5.4913abc | 86.5a |
| Pullulanase | NGNS2hr | 227.50a | 135.06a | 92.44c | 318.63a | 91.1ab | 183.56a | 5.9312abc | 86.7a |
| | NGNS4hr | 247.54a | 135.77a | 111.77b | 303.6a | 56.1ab | 167.83a | 5.9151abc | 83.63b |
| | NGNS16hr | 223.63a | 92.04a | 131.58a | 223.02a | −0.60b | 130.98a | 5.7031abc | 83.81b |
| | GNS2hr | 6.35b | 4.29b | 1.88d | 4.81b | ND | ND | 3.7061cd | ND |
| | GNS4hr | 4.9b | 3.63b | 1.10d | 4.4b | ND | ND | 3.9263bcd | ND |
| | GNS16hr | 6.83b | 5.29b | 1.63d | 8.73b | 1.90b | 3.44b | 6.4278a | ND |
| | GS2hr | 7.64b | 6.75b | 0.89d | 9.64b | 2.00b | 2.89b | 5.8659abc | ND |
| | GS4hr | 8.71b | 7.58b | 1.13d | 11.21b | 2.5b | 3.62b | 5.8168abc | ND |
| | GS16hr | 6.75b | 5.33b | 1.5d | 7.42b | ND | 2.08b | 6.2895ab | ND |

[1]Abbreviations: PV = Peak Viscosity; MV = Minimum Viscosity; BKD = Break down; FV = Final Viscosity; SBK = Set back; TSB = Total Set Back; TP = Time to Peak; PT = Pasting Temperature; ND = non-detectable.
[2]Units: Viscosity (RVU); Temperature (° C.); Time (min)
[3]Means with different letters within each column are significantly different at $p \leq 0.05$. The values are an average of 2 to 4 measures.

EXAMPLE 10

Effect of α-Amylase Treatment on Pasting Characteristics of Rice Flour

No significant pasting was seen in any of the treatments. Even the non-gelatinized (NGNS) samples had little pasting qualities due to the high temperature (75° C.) of incubation with α-amylase, a temperature that will gelatinize flour (Table 9; graphs of viscosity not shown). There were no significant differences in the PV, MV, BKD, FV, SBK, TSB, and TP among the NGNS, GNS, and GS treatments and the commercial control (Table 9).

The NGNS2 hr and 16 hr samples had a pasting peak at 4.4 min with PV of 7.56 and 8.61 RVU. The BKD values were 4.61 and 5.06 RVU, respectively, indicating some breakdown in viscosity during the cooking process. For NGNS4 hr, no increase in viscosity was seen during cooking. It is unclear why the NGNS2 hr and 16 hr treatments, one shorter and one longer than NGNS4 hr, had small pasting peaks. The TP for all the treatments ranged from 2.48 to 6.62 min. Only the NGNS2 hr and 16 hr enzyme-treated samples had peaks large enough to indicate a breakdown. The rest of the samples had already been cooked and PT was not detected.

The α-amylase treated rice flour would not be suitable as an ingredient in viscous food products due to the minimal pasting characteristics.

already gelatinized, no pasting temperatures were detected. The NGNS2 hr and NGNS16 hr samples also had no pasting temperatures, and only one replicate of NGNS4 hr had a PT at 81.5° C. Since only one NGNS4 hr replicate showed pasting, the average reported in Table 10 is distorted due to dividing 81.5° C. by four replicates.

The NGNS2 hr and 4 hr samples had significantly lower pasting abilities than untreated rice flour (p≦0.05) (Table 10). The NGNS samples had a peak at 3.75 and 3.88 min with PV at 10.9 and 11.5 RVU, respectively. There was a small amount of breakdown as measured by MV being one-third of PV for the two samples.

The α-amylase-pullulanase treated NGNS samples had significantly lower pasting qualities than the NGNS samples treated with only pullulanase. It is possible that the higher incubation temperature for the α-amylase-pullulanase treatment was responsible for part of the difference. It is also possible that α-amylase degraded the starch so the sample could not paste like untreated rice flour. The NGNS16 hr, GNS and GS samples were almost identical to each other in

TABLE 9

Effects of Gelatinization Storage and Incubation Duration on Pasting Characteristics of α-amylase Treated Rice Flour[1,2,3]

| Sample | Treatment | PV | MV | BKD | FV | SBK | TSB | TP | PT |
|---|---|---|---|---|---|---|---|---|---|
| Control | — | 5.75b[3] | 4.42cd | ND | 4.92cde | ND | ND | 2.28b | ND |
| Rice Flour | — | 236a | 155a | 81.2a | 377a | 141a | 223a | 5.49ab | 86.5a |
| α-Amylase | NGNS2hr | 7.56b | 2.94d | 4.61b | 3.56e | −4.00b | ND | 4.42ab | ND |
|  | NGNS4hr | 5.17b | 3.71cd | ND | 4.00ed | ND | ND | 4.45ab | ND |
|  | NGNS16hr | 8.61b | 3.56cd | 5.06b | 4.03ed | −4.58b | ND | 4.41ab | ND |
|  | GNS2hr | 5.15b | 4.25cd | ND | 4.79cde | ND | ND | 5.17ab | ND |
|  | GNS4hr | 4.83b | 4.25cd | ND | 4.81cde | ND | ND | 5.30ab | ND |
|  | GNS16hr | 5.53b | 4.92cd | ND | 5.94bcd | ND | 1.03b | 6.62a | ND |
|  | GS2hr | 8.88b | 7.17b | ND | 8.04b | ND | ND | 2.48ab | ND |
|  | GS4hr | 7.29b | 5.58bc | ND | 6.5bc | ND | ND | 6.26ab | ND |

[1] Abbreviations: PV = Peak Viscosity; MV = Minimum Viscosity; BKD = Break down; FV = Final Viscosity; SBK = Set back; TSB = Total Set Back; TP = Time to Peak; PT = Pasting Temperature; ND = non-detectable.
[2] Units: Viscosity (RVU); Temperature (° C.); Time (min)
[3] Means with different letters within each column are significantly different at $p \leq 0.05$. The values are an average of 2 to 4 measures.

EXAMPLE 11

Effect of α-Amylase-Pullulanase Treatment on Pasting Characteristics of Rice Flour For the samples incubated with both α-amylase and pullulanase, no significant difference was found between the commercial control and the NGNS samples in pasting characteristics in PV, MV, BKD, FV, SBK, TSB and TP (Table 10, viscosity figures not shown). The temperature for enzyme incubation was 60° C. for all treatments. No significant differences was seen between the gelatinized samples and the commercial control. NGNS2 hr and NGNS4 hr samples had 5.6 and 6.8 RVU in BKD, the only detectable BKD besides the native rice flour. Since the GNS and GS samples were the RVA analysis, but were significantly different from the untreated rice flour (Table 10). None of these samples had an increase in viscosity, and therefore no BKD, SBK and TSB was detected. Due to the lack of pasting in these samples, they are not suitable for food products that are highly viscous.

The post-cooking viscosity of all NGNS samples was not significantly different from the commercial control. There was no increase in FV in any treated samples, whereas the FV for untreated rice flour was the highest reading among all samples. The only reported PT was for NGNS4 hr. The TP for all treatments were not significantly different from the commercial control and untreated rice flour. The time to peak values were between 2.25 to 5.82 min.

TABLE 10

Effects of Gelatinization/Storage and Incubation Duration on Pasting Characteristics of α-Amylase-Pullulanase Treated Rice Flour[1,2,3]

| Sample | Treatment | PV | MV | BKD | FV | SBK | TSB | TP | PT |
|---|---|---|---|---|---|---|---|---|---|
| Control | — | 5.75bc | 4.42b | ND | 4.92b | ND | ND | 2.28a | ND |
| Rice Flour | — | 236a | 155a | 81.2a | 377a | 141a | 223a | 5.49a | 86.5a |

TABLE 10-continued

Effects of Gelatinization/Storage and Incubation Duration on
Pasting Characteristics of α-Amylase-Pullulanase Treated Rice Flour[1,2,3]

| Sample | Treatment | PV | MV | BKD | FV | SBK | TSB | TP | PT |
|---|---|---|---|---|---|---|---|---|---|
| α-Amylase-Pullulanase | NGNS2hr | 10.9bc | 3.88b | 5.60bc | 4.42b | −6.50cd | ND | 3.75a | ND |
|  | NGNS4hr | 11.5b | 3.79b | 6.83b | 4.27b | −7.25d | ND | 3.88a | 20.4a |
|  | NGNS16hr | 4.88c | 4.00b | ND | 4.46b | ND | ND | 3.60a | ND |
|  | GNS2hr | 5.25c | 4.42b | ND | 4.92b | ND | ND | 4.19a | ND |
|  | GNS4hr | 5.08c | 4.71b | ND | 5.33b | ND | ND | 5.82a | ND |
|  | GNS16hr | 5.92bc | 5.08b | ND | 5.21b | ND | ND | 3.89a | ND |
|  | GS2hr | 5.29c | 3.54b | ND | 4.29b | ND | ND | 2.25a | ND |
|  | GS4hr | 5.92bc | 4.79b | ND | 5.21b | ND | ND | 5.44a | ND |

[1] Abbreviations: PV = Peak Viscosity; MV = Minimum Viscosity; BKD = Break down; FV = Final Viscosity; SBK = Set back; TSB = Total Set Back; TP = Time to Peak; PT = Pasting Temperature; and ND = non-detectable.
[2] Units: Viscosity (RVU); Temperature (° C.); Time (min)
[3] Means with different letters within each column are significantly different at $p \leq 0.05$. The values are an average of 2 to 4 measures.

EXAMPLE 12

Effects of Pullulanase Treatment on Pasting Characteristics of Rice Starch

Figure 5:
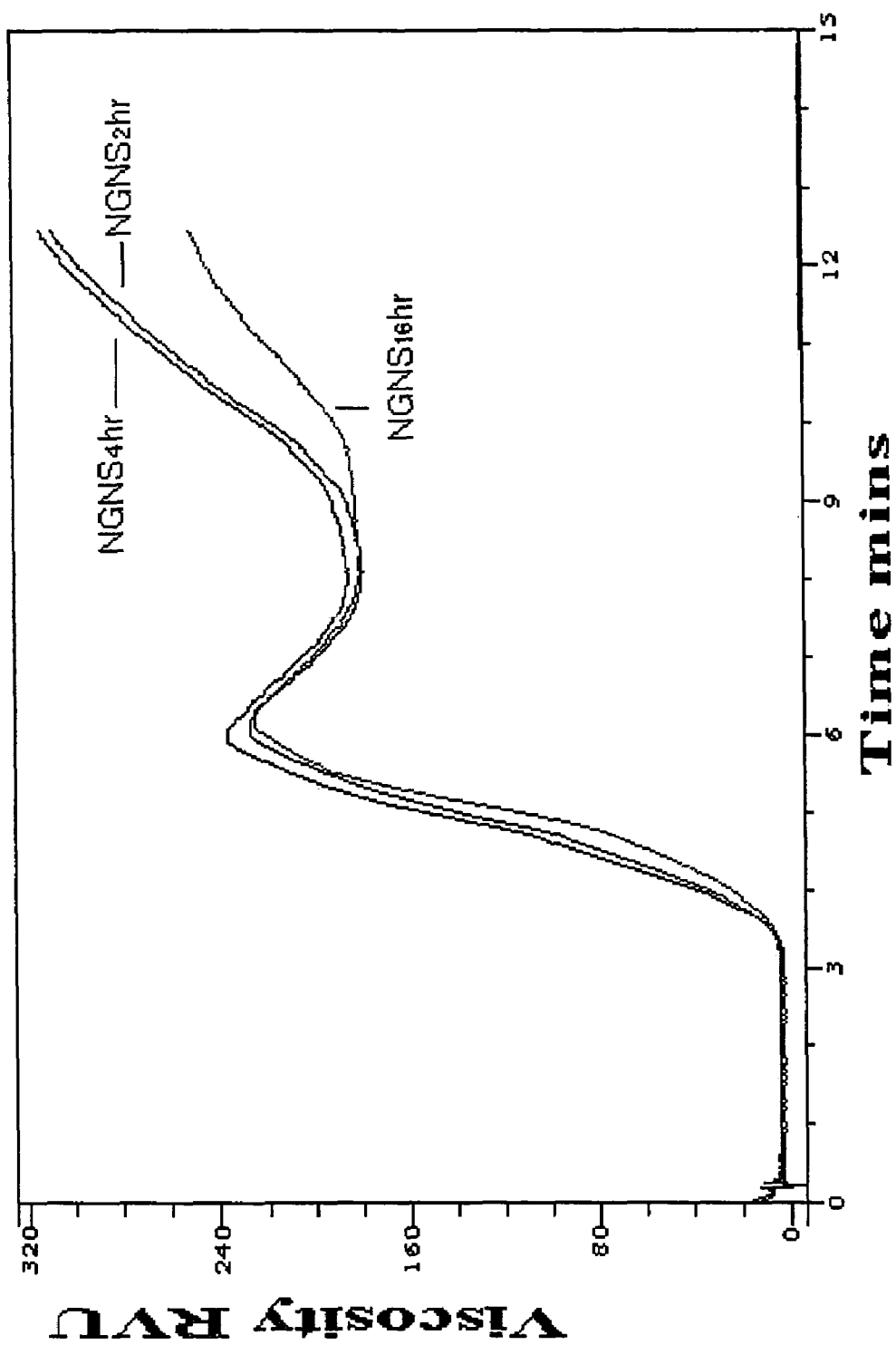
FIG. 5 illustrates the results of rapid visco amylograph analysis of non-gelatinized rice starch that was not stored before being incubated with the enzyme pullulanase for either 2 hr (NGNS2 hr), 4 hr (NGNS4 hr), or 16 hr (NGNS16 hr).

For pullulanase-treated rice starch, the pasting activity in the NGNS (2, 4, 16 hr) samples was similar (Table 11), but was significantly greater ($p \leq 0.05$) than the commercial control. NGNS treatment increased the PV by 30-48 RVU as compared to untreated rice starch, with the NGNS4 hr sample having the greatest difference at 48 RVU (FIGS. 1 and 5). There was twice as much BKD in the NGNS samples than in the untreated rice starch. Pasting temperature was in a similar range, approximately 80° C. Within the NGNS treatments, the 16 hr treatment had the lowest SBK and TSB, 30 to 40 RVU lower than the 2 hr and 4 hr treatments.

Figure 6:
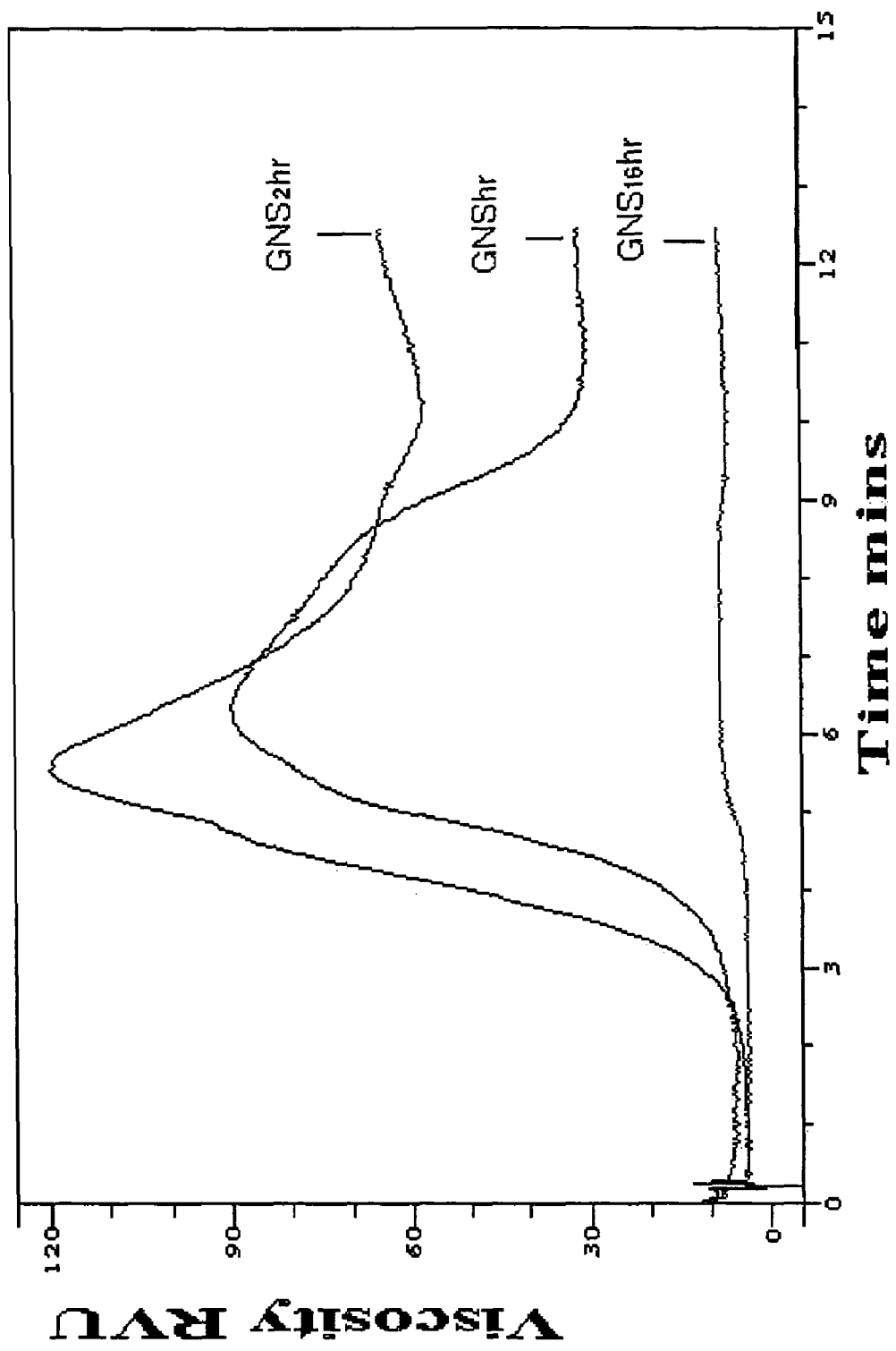
FIG. 6 illustrates the results of rapid visco amylograph analysis of gelatinized rice starch that was not stored before being incubated with pullulanase for either 2 hr (GNS2 hr), 4 hr (GNS4 hr), or 16 hr (GNS16 hr).

The GNS2 hr and 4 hr treatments showed some pasting activity (Table 11, FIG. 6). There was a decrease in PV, MV and FV as the incubation time increased. GNS4 hr had the highest BKD (54.54 RVU) and PT (89.62° C.) among the three GNS treatments.

Figure 7:
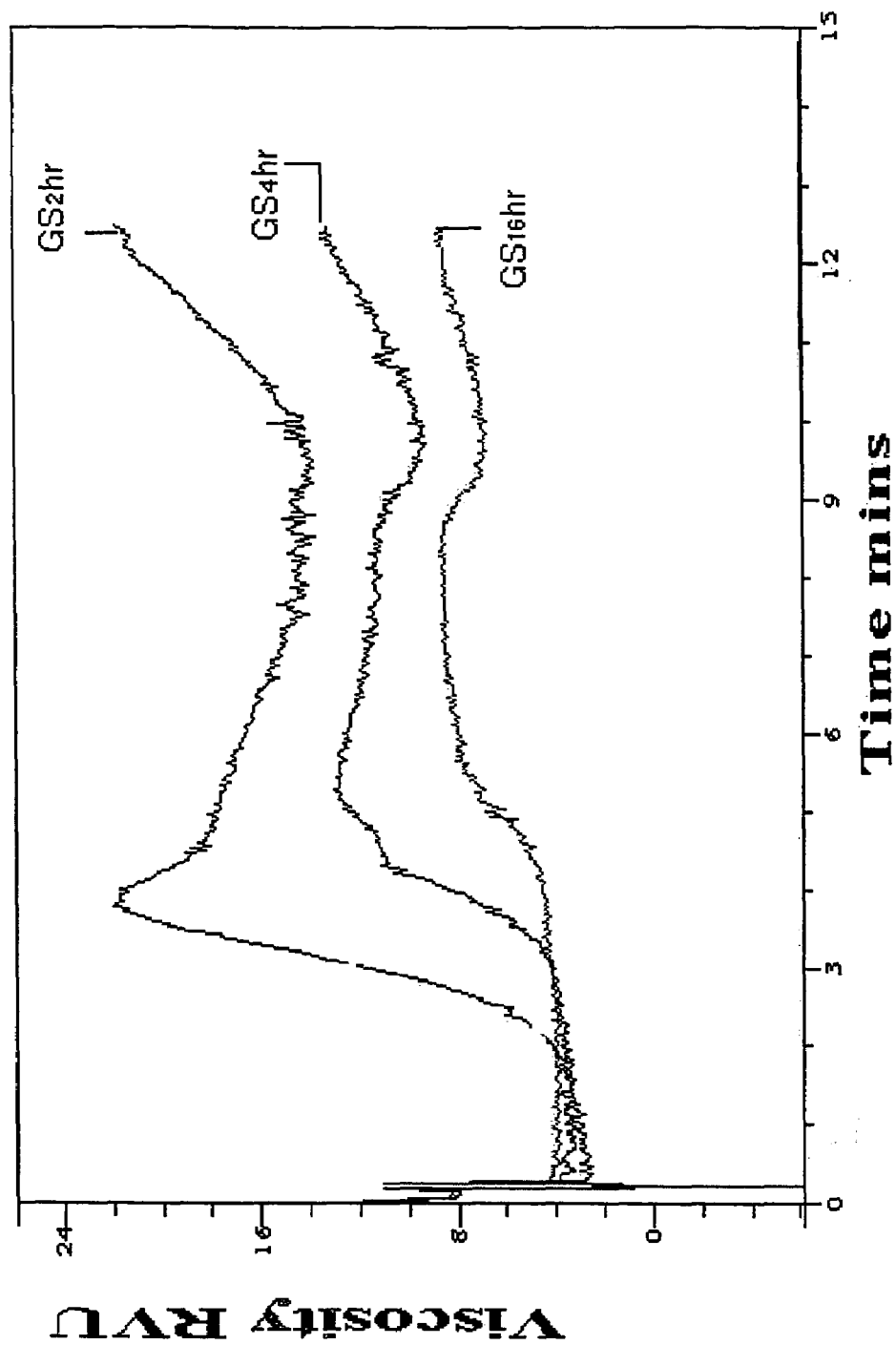
FIG. 7 illustrates the results of rapid visco amylograph analysis of gelatinized rice starch that was stored overnight before being incubated with pullulanase for either 2 hr (GS2 hr), 4 hr (GS4 hr), or 16 hr (GS16 hr).

There was a progressive decrease in pasting properties among the NGNS, GNS and GS samples. (FIGS. 5, 6, and 7) The NGNS samples had the highest pasting characteristics, similar to that of the untreated rice starch. The NGNS samples had slightly higher values for PV, MV, and FV as compared to the untreated rice starch. GNS16 hr and the GS treatments were significantly lower ($p \leq 0.05$) than the untreated rice starch in PV, MV, FV, BKD, SBK and TSB (Table 11; FIGS. 1, 6, and 7). The SBK and TSB of the GNS and GS treated samples were not significantly different from the commercial control. GS2 hr and GS4 hr had 6.33 and 2.63 RVU in BKD, and 6.94 and 3.15 RVU in TSB, respectively. SBK was not detected. The GNS-treated samples had decreasing pasting characteristics as incubation time increased, and were significantly lower than the untreated rice starch (Table 11, FIGS. 1 and 6). The GNS2 hr sample had the best pasting properties among the three GNS samples, followed by GNS4 hr and then GNS16 hr. The FV values for all three samples were lower than the PV. The BKD for the NGNS sample was higher than the untreated rice starch, 23 to 31 RVU higher. GNS 16 hr had no pasting activity and had no breakdown, and was similar to the GS treatments. The general trend of all the pullulanase treatments was the longer the incubation, the lesser the pasting qualities.

The GS treated rice starch had significantly less pasting than the untreated rice starch. The highest PV was only 22.8RVU in the GNS2 hr sample. BKD ranged from 0 to 6.33 RVU, SBK was not detectable, and TSB was 3.15 to 6.94 RVU.

The NGNS samples had the highest retrogradation potential as they had the largest TSB and SBK values while GNS had the lowest. The NGNS and GNS2 hr and 4 hr samples also had the highest BKD values indicating a greater disruption of starch granules during cooking.

The treated rice flour took a shorter time to cook than the treated rice starch. The highest TP was 6.25 min in the NGNS16 hr sample. The NGNS, and GNS2 hr samples had similar PT ($p > 0.05$, Table 11) to untreated rice flour, 79 to 84.5° C. The GNS2 hr and GNS4 hr samples were not significantly different from each other in PT, 84.5 and 89.6° C., respectively. The GNS16 hr and GS samples showed no pasting, and were not significantly different from the commercial control.

TABLE 11

Effects of Gelatinization/Storage and Incubation Duration on
Pasting Characteristics of Pullulanase Treated Rice Starch[1,2,3]

| Sample | Treatment | PV | MV | BKD | FV | SBK | TSB | TP | PT |
|---|---|---|---|---|---|---|---|---|---|
| Control | — | 5.75d | 4.42c | 0d | 4.92c | 0c | 0c | 2.28f | ND |
| Rice Starch | — | 198.13b | 174.67a | 23.46bc | 271.08b | 73.0a | 96.4ab | 6.32abc | 81.23b |
| Pullulanase | NGNS2hr | 234.73ab | 186.67a | 48.06a | 296.44ab | 61.7a | 110a | 6.07bc | 79.03b |
|  | NGNS4hr | 246.9a | 196.13a | 50.770a | 316.15a | 69.3a | 120a | 6.11bc | 80.14b |
|  | NGNS16hr | 232.02ab | 189.29a | 42.73ab | 265.52b | 33.5b | 76.2b | 6.25bc | 81.55b |
|  | GNS2hr | 88.83c | 42.31b | 46.52ab | 46.94c | −41.9d | 3.63c | 5.87cd | 84.54ab |
|  | GNS4hr | 82.73c | 28.19bc | 54.54a | 29.98c | −52.8d | 0c | 6.42ab | 89.62a |

TABLE 11-continued

Effects of Gelatinization/Storage and Incubation Duration on
Pasting Characteristics of Pullulanase Treated Rice Starch[1,2,3]

| Sample | Treatment | PV | MV | BKD | FV | SBK | TSB | TP | PT |
|---|---|---|---|---|---|---|---|---|---|
| | GNS16hr | 8.33d | 6.79c | 0d | 7.92c | 0c | 0c | 6.84a | ND |
| | GS2hr | 22.81d | 15.67bc | 6.33cd | 22.60c | 0c | 6.94c | 3.76e | ND |
| | GS4hr | 12.83d | 10.21c | 2.63cd | 13.35c | 0c | 3.15c | 5.40d | ND |
| | GS16hr | 8.6d | 7.69c | 0d | 8.27c | 0c | 0c | 6.78a | ND |

[1]Abbreviations: PV = Peak Viscosity; MV = Minimum Viscosity; BKD = Break down; FV = Final Viscosity; SBK = Set back; TSB = Total Set Back; TP = Time to Peak; PT = Pasting Temperature; and NO = non-detectable.
[2]Units: Viscosity (RVU); Temperature (° C.); Time (min)
[3]Means with different letters within each column are significantly different at $p \leq 0.05$. The values are an average of 2 to 4 measures.

EXAMPLE 13

Effects of α-Amylase Treatment on Pasting Characteristics of Rice Starch

There was insufficient sample in the GS (all) and GNS (4, 16 hr) treatments to conduct RVA analysis. The GS2 hr and NGNS (4, 16 hr) treated samples were not significantly different from the commercial control in PV, MV, FV, SBK, TSB and PT (Table 12; no viscosity figures shown). The NGNS samples had pasting activity at 80 to 84° C., and took about 3.9 to 4.4 min to reach the pasting peak. This time is less than the TP for untreated rice starch, 6.3 min ($p \leq 0.05$). The BKD for the NGNS2 hr sample was greater than the untreated rice starch ($p \leq 0.05$), while the NGNS4 hr and 16 hr samples were not significantly greater than the untreated rice starch in BKD (Table 12). There was considerable amount of BKD in the NGNS treated samples as the MV and FV were 4.6 to 6.58 RVU. The untreated rice starch had better cooking stability than the NGNS treated samples. The NGNS and GNS2 hr treated samples had SBKs from −95.3 to 73 RVU, and no TSB since the FV was much lower than the PV (Table 12). The GNS2 hr sample did not have a PT, probably because the sample had been gelatinized prior to enzyme treatment.

EXAMPLE 14

Effects of α-Amylase-Pullulanase Treatment on Pasting Characteristics of Rice Starch There was insufficient sample from NGNS16 hr, GNS (all) and GS16 hr treatments to collect pasting characteristic data on them. All the variables except BKD examined for GS and NGNS treatments were significantly lower than values for the untreated rice starch, but were similar to the commercial control (Table 13, viscosity figures not shown). There was no breakdown, setback, and total setback in the GS2 hr and GS4 hr samples. The NGNS2 hr and NGNS4 hr samples had 18 RVU for PV, 3 RVU for MV and 14 RVU for BKD (Table 13). The NGNS samples showed less breakdown than in the untreated rice starch. All the samples had very low FV, which resulted in 0 values for TSB.

The effects of α-amylase-pullulanase treatment on rice flour and starch were very similar. Although the samples had very low or zero values for SBK, TSB and BKD which indicates stability during cooking (Tables 10 and 13), these products would not be recommended for use in viscous food products because the pasting viscosities were low.

TABLE 12

Effects of Gelatinization/Storage and Incubation Duration on
Pasting Characteristics of α-Amylase Treated Rice Starch[1,2,3]

| Sample | Treatment | PV | MV | BKD | FV | SBK | TSB | TP | PT |
|---|---|---|---|---|---|---|---|---|---|
| Control | — | 5.75c | 4.4167b | 0b | 4.917b | 0b | 0b | 2.2811d | ND |
| Rice Starch | — | 198.13a | 174.6667a | 23.46b | 271.083a | 73.0a | 96.42a | 6.3224b | 81.225a |
| α-Amylase | NGNS2hr | 100.98b | 4.1875b | 96.79a | 5.67b | −95.3c | 0b | 4.1225b | 80.663a |
| | NGNS4hr | 67.13bc | 3.8550b | 63.27ab | 4.605b | −62.5bc | 0b | 3.8850b | 80.35a |
| | NGNS16hr | 69.46bc | 4.415b | 65.04ab | 6.583b | 62.9bc | 0b | 4.4325b | 84.113a |
| | GNS2hr | 7.67c | 3.5b | 3.46b | 4.667b | −3.00b | 0b | 3.1278c | ND |

[1]Abbreviations: PV = Peak Viscosity; MV = Minimum Viscosity; BKD = Break down; FV = Final Viscosity; SBK = Set back; TSB = Total Set Back; TP = Time to Peak; PT = Pasting Temperature; and ND = non-detectable
[2]Units: Viscosity (RVU); Temperature (° C.); Time (min)
[3]Means with different letters within each column are significantly different at $p \leq 0.05$. The values are an average of 2 to 4 measures.

TABLE 13

Effects of Gelatinization/Storage and Incubation Duration on Pasting Characteristics of α-Amylase-Pullulanase Treated Rice Starch[1,2,3]

| Sample | Treatment | PV | MV | BKD | FV | SBK | TSB | TP | PT |
|---|---|---|---|---|---|---|---|---|---|
| Control | — | 5.75b | 4.42b | 0b | 4.92b | 0b | 0b | 2.28d | ND |
| Rice Starch | — | 198a | 175a | 23.5a | 271a | 73.0a | 96.4a | 6.32a | 81.2a |
| α-Amylase-Pullulanase | NGNS2hr | 18.2b | 3.52b | 14.6ab | 4.13b | −14.0b | 0b | 3.83b | 60.6a |
|  | NGNS4hr | 17.4b | 3.71b | 13.7ab | 4.40b | −13.0b | 0b | 3.99b | 40.7a |
|  | GS2hr | 5.83b | 3.08b | 0b | 3.58b | 0b | 0b | 2.44c | ND |
|  | GS4hr | 6.25b | 5.13b | 0b | 5.63b | 0b | 0b | 6.45a | ND |

[1]Abbreviations: PV = Peak Viscosity; MV = Minimum Viscosity; BKD = Break down; FV = Final Viscosity; SBK = Set back; TSB = Total Set Back; TP = Time to Peak; PT = Pasting Temperature; and ND = non-detectable.
[2]Units: Viscosity (RVU); Temperature (° C.); Time (min)
[3]Means with different letters in each column are significantly different ($p \leq 0.05$). The values are an average of 4 measurements.

In rice starch, the effects of the enzymes treatments on the pasting properties were complex due to the different temperatures used during incubation. The target linkages of pullulanase and α-amylase also resulted in different end products. Pullulanase debranches the starch molecules, while α-amylase cleaves randomly within the starch molecules. The longer chained molecules left from pullulanase debranching were able to paste better as observed in the RVA analysis. The α-amylase-treated samples had little pasting properties due to random cleaving of the starch molecules, in addition to the higher incubation temperature (75° C.) required for optimum enzyme activity. The high incubation temperature was within the range of starch gelatinization temperatures. Therefore during RVA analysis, the α-amylase samples did not display significant pasting properties even when the sample had not been gelatinized prior to enzyme treatment. The α-amylase-pullulanase samples had very similar pasting properties to the α-amylase treated samples, probably due to the synergistic effects of α-amylase and pullulanase in digesting the starch molecules. Most of the starch molecules had been degraded into simple sugars which do not paste like untreated rice flour and starch.

Due to the absence or low availability of lipids and proteins, the untreated rice starch had slightly different pasting properties than untreated rice flour. There was a greater potential for retrogradation in rice flour as seen in FIG. 5, probably due to the presence of lipids. However, in GNS-pullulanase treated rice flour, there was virtually no increase in viscosity during cooking or holding temperature, while the same treatment on rice starch produced significant pasting upon cooking and retrogradation during storage (FIGS. 3 and 6). In the GS-pullulanase treated rice flour, the PV, MV, FV and TSB were not as pronounced as the GS-pullulanase treated rice starch.

In the NGNS treated rice starch and flour, the pullulanase-treated sample had the best pasting properties. The α-amylase treatment on NGNS rice starch resulted in greater PV values than the α-amylase-pullulanase treated NGNS rice starch. However, both had no cooking stability as the MV values were similar to the viscosity detected prior to PV. The NGNS rice flour and rice starch treated with α-amylase and α-amylase-pullulanase were very similar in pasting properties. There was pasting observed during heating, however the peak rapidly disappeared as the temperature was held at 95° C.

The pasting qualities of both rice starch and flour samples changed according to enzyme and incubation temperature. Samples treated with pullulanase, regardless of gelatinization and storage state, had higher PV, MV and FV, probably because these samples were incubated at 55° C., thus not exceeding the pasting temperature of 60-78° C. In addition, pullulanase is a debranching enzyme as opposed to α-amylase, which randomly cleaves α (1,4) glycosidic bonds. There was greater degradation in the samples when α-amylase was used; both α-amylase and α-amylase-pullulanase treatments had lower pasting qualities. The samples that were gelatinized displayed little or no pasting qualities as expected. The NGNS rice starch samples treated with pullulanase had slightly higher PV, FV and BKD than the untreated rice starch. The NGNS pullulanase treated rice flour samples had very similar pasting qualities as the untreated rice flour.

Only the NGNS samples on flour and starch that were treated with pullulanase retained their pasting characteristics. Resistant starch produced by this method would be more suitable for manufacturing food products with high viscosity after cooking than the commercial CrystaLean®.

Heating Profiles of Enzyme Treated Rice Starch and Rice Flour as Detected by Differential Scanning Calorimetry (DSC)

Differential Scanning Calorimetry (DSC) measures heat absorbed or given off by a sample in a controlled atmosphere at specified temperatures. DSC provides information about a specific heat and latent heat of samples as temperature rises, which indicates changes in the amorphous and crystalline structures. Data is recorded in terms of heat flow, and is presented in joules/gram (J/g). (Cassel, 2002) In the analysis of starch, starch gelatinization parameters such as peak onset, peak temperature, end of peak, and gelatinization enthalpy information is collected. DSC can detect the presence of resistant starch in samples. RS was found to give endothermic peaks between 136 to 162° C., while amylose-lipid complexes exhibited peaks at 95-130° C. (Sievert and Pomeranz, 1989).

EXAMPLE 15

Differential Scanning Calorimetry (DSC) Materials and Methods

Samples of resistant starch were prepared as described in Example 1. Differential Scanning Calorimetry (DSC) was conducted to measure specific and latent heat which indicates structural changes from amorphous to crystalline. DSC was measured in a model Q100, TA Instruments (New Castle, Del.). DSC Pans were purchased from TA Instruments (Part no. 900825.902, T21230; New Castle, Del.). A 10 mg sample was placed in the pan, and 20 mg water added. The pan was sealed, and the samples equilibrated overnight at room temperature. During analysis, the sample was heated at 35° C. for five minutes, and then heated to 140° C. at a rate of 5° C./min. Samples that indicated peaks beyond the gelatinization temperature range, 60-80° C., were reheated to determine the stability of the peaks. Four replicates were analyzed for each treatment.

Statistical analyses were conducted using SAS software (version 8.0) as described in Example 1. Post-hoc multiple comparisons were performed using Tukey's studentized range test to test the interactions of incubation periods and gelatinization type in enzyme treated rice flour and starch, and the effects on peak onset, peak, and end of peak temperatures. Abbreviations for sample preparation are as described above: GS for gelatinization with storage, NGNS for no gelatinization without storage, GNS for gelatinization without storage, RF for rice flour, and RS for rice starch.

EXAMPLE 16

Effects of Pullulanase Treatment on Heating Profile of Rice Flour

The commercial control, CrystaLean®, was analyzed by DSC along with the samples and untreated rice flour. The commercial control had no gelatinization activity at normal temperatures, indicating prior gelatinization (Table 14, FIG. 8).

Figure 8:
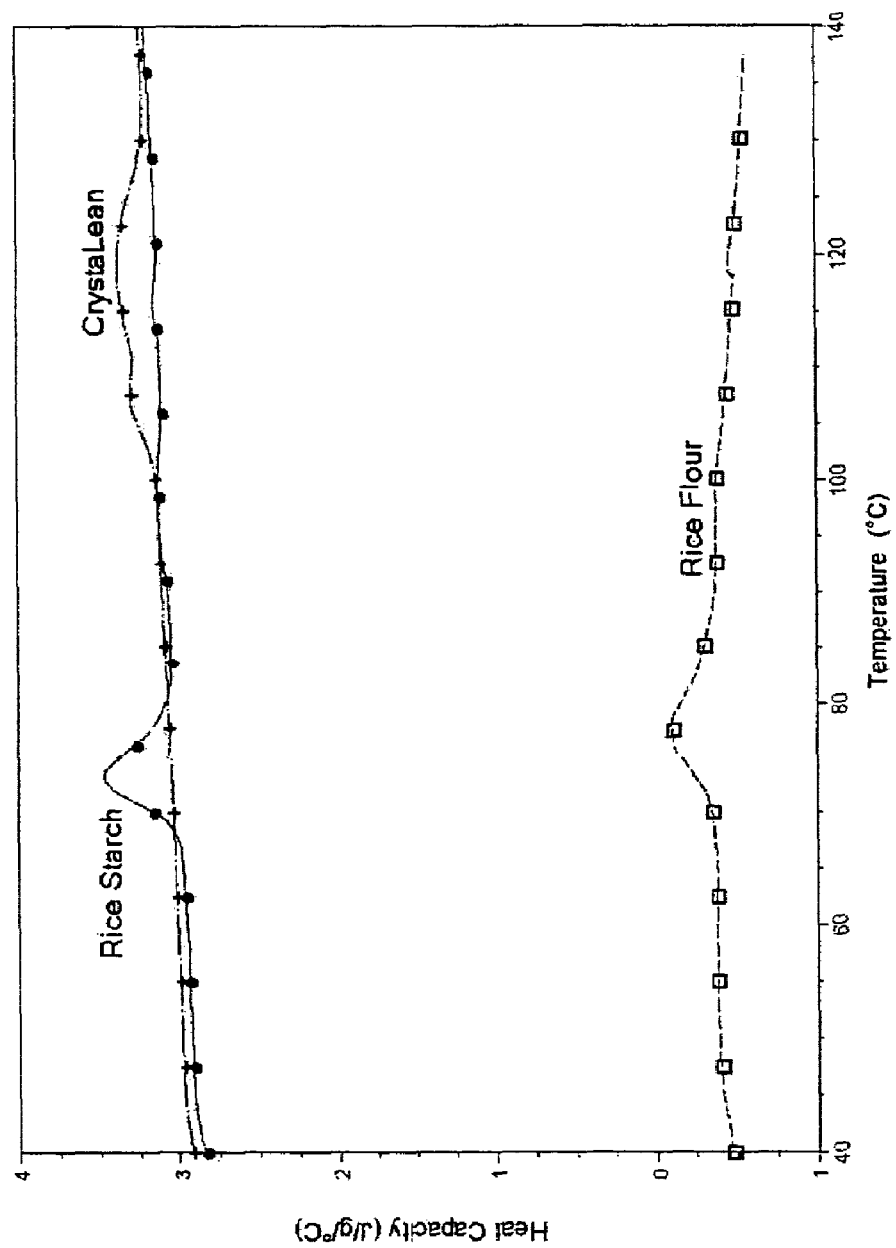
FIG. 8 illustrates the results of differential scanning calorimetry on untreated rice flour, untreated rice starch, and a commercial resistant starch, CrystaLean®.
Figure 9:
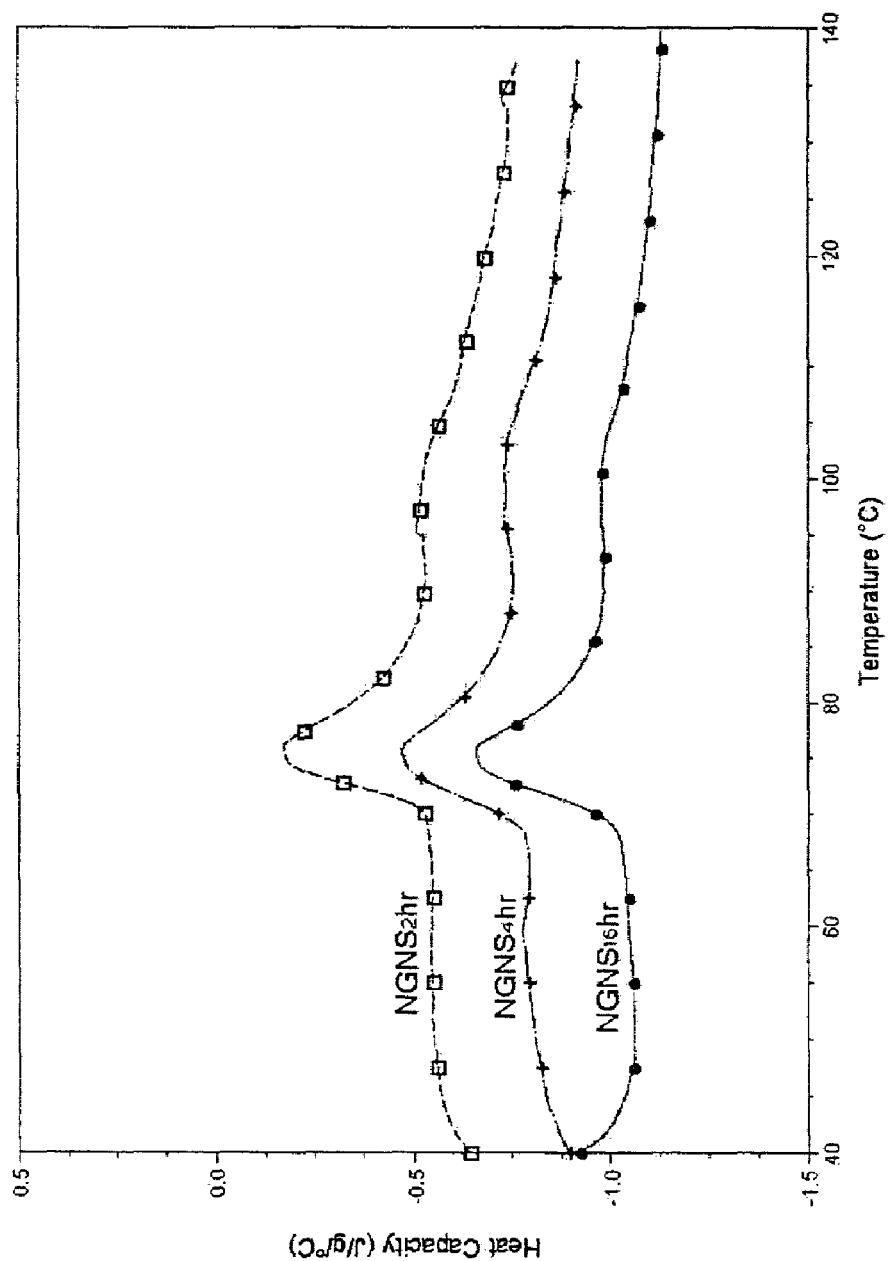
FIG. 9 illustrates the results of differential scanning calorimetry of non-gelatinized rice flour that was not stored before being incubated with the enzyme pullulanase for either 2 hr (NGNS2 hr), 4 hr (NGNS4 hr), or 16 hr (NGNS16 hr).

The NGNS-treated samples were not significantly different from the untreated rice flour for gelatinization, amylose-lipid complex, and resistant starch peaks (Table 14; FIGS. 8 and 9). For the untreated rice flour, the enthalpy for the gelatinization peak was 2.85 J/g. The enthalpy required to produce the gelatinization peak in the NGNS treated samples was 10 to 15 times higher than the untreated rice flour (Table 14). A higher peak enthalpy means that a greater amount of energy was required to produce the peak. The starch granules within the sample may be more compact and more resistant to cooking. There was no significant difference in the other treated samples and the untreated rice flour in peak onset, peak, and completion temperatures, and enthalpy. The temperature ranges for gelatinization peak onset was 49.0 to 71.9° C., peak was 57 to 81.1° C. and completion was 69.6 to 98.0° C. (Table 14). The enthalpy range was between 0.18 and 41.9 J/g.

For the amylose-lipid complex peak, the peak onset temperatures ranged from 76.3 to 101° C. The commercial control did not have a peak. The peak onset temperature for the GNS16 hr treated sample was significantly lower ($p \leq 0.05$) than the untreated rice flour (FIGS. 8 and 10; Table 14). The GNS2 hr and 4 hr treated samples had significantly higher ($p \leq 0.05$) peak onset temperatures than GNS16 hr and GS16 hr. No significant difference was seen in the completion temperatures and peak enthalpies between any sample and the untreated rice flour.

TABLE 14

Effects of Gelatinization/Storage and Incubation Duration on Thermal Characteristics of Pullulanase Treated Rice Flour[1,2,3]

| Sample | Treatment | First Transition (Gelatinization) | | | | Second Transition (Amylose-lipid complex) | | | | Third Transition (Resistant Starch) | | | |
|---|---|---|---|---|---|---|---|---|---|---|---|---|---|
| | | $T_O$ | $T_P$ | $T_C$ | ΔH | $T_O$ | $T_P$ | $T_C$ | ΔH | $T_O$ | $T_P$ | $T_C$ | ΔH |
| Control | — | ND | ND | ND | ND | ND | ND | ND | ND | 101a | 119a | 133a | 3.69a |
| Rice Flour | — | 70.9a | 77.8a | 92a | 2.85a | 94.2ab | 100abc | 106a | 0.184a | 118a | 119a | 128a | 0.172b |
| Pullulanase | NGNS2hr | 68.9a | 76.2a | 90.7a | 31.64a | 98.0a | 103ab | 110a | 2.19a | 124a | 126a | 129a | 0.519b |
| | NGNS4hr | 63.0a | 69.9a | 90.3a | 38.7a | 91.9abc | 98.4abc | 107a | 1.45a | ND | ND | ND | ND |
| | NGNS16hr | 63.4a | 69.7a | 88.6a | 41.9a | 93.8abc | 101abc | 111a | 12.8a | 120a | 121a | 127a | 0.0159b |
| | GNS2hr | 51.8a | 61.5a | 70.5a | 0.51a | 101a | 109a | 121a | 1.03a | ND | ND | ND | ND |
| | GNS4hr | 71.9a | 81.1a | 91.8a | 0.44a | 101a | 110a | 123a | 0.896a | ND | ND | ND | ND |
| | GNS16hr | 51.3a | 74.3a | 98.0a | 4.15a | 78.3bc | 90.1bc | 107a | 1.50a | 114a | 120a | 130a | 0.235b |
| | GS2hr | 49.0a | 60.9a | 83.9a | 3.43a | 89.3abc | 97.3abc | 108a | 0.801a | 111a | 114a | 122a | 0.187b |
| | GS4hr | 54.9a | 62.2a | 77.6a | 0.75a | 88.4abc | 95.1bc | 107a | 0.652a | 108a | 113a | 124a | 0.363b |
| | GS16hr | 51..2a | 57.0a | 69.6a | 0.18a | 76.3c | 88.1c | 105a | 2.78a | 106a | 111a | 119a | 0.131b |

Figure 10:
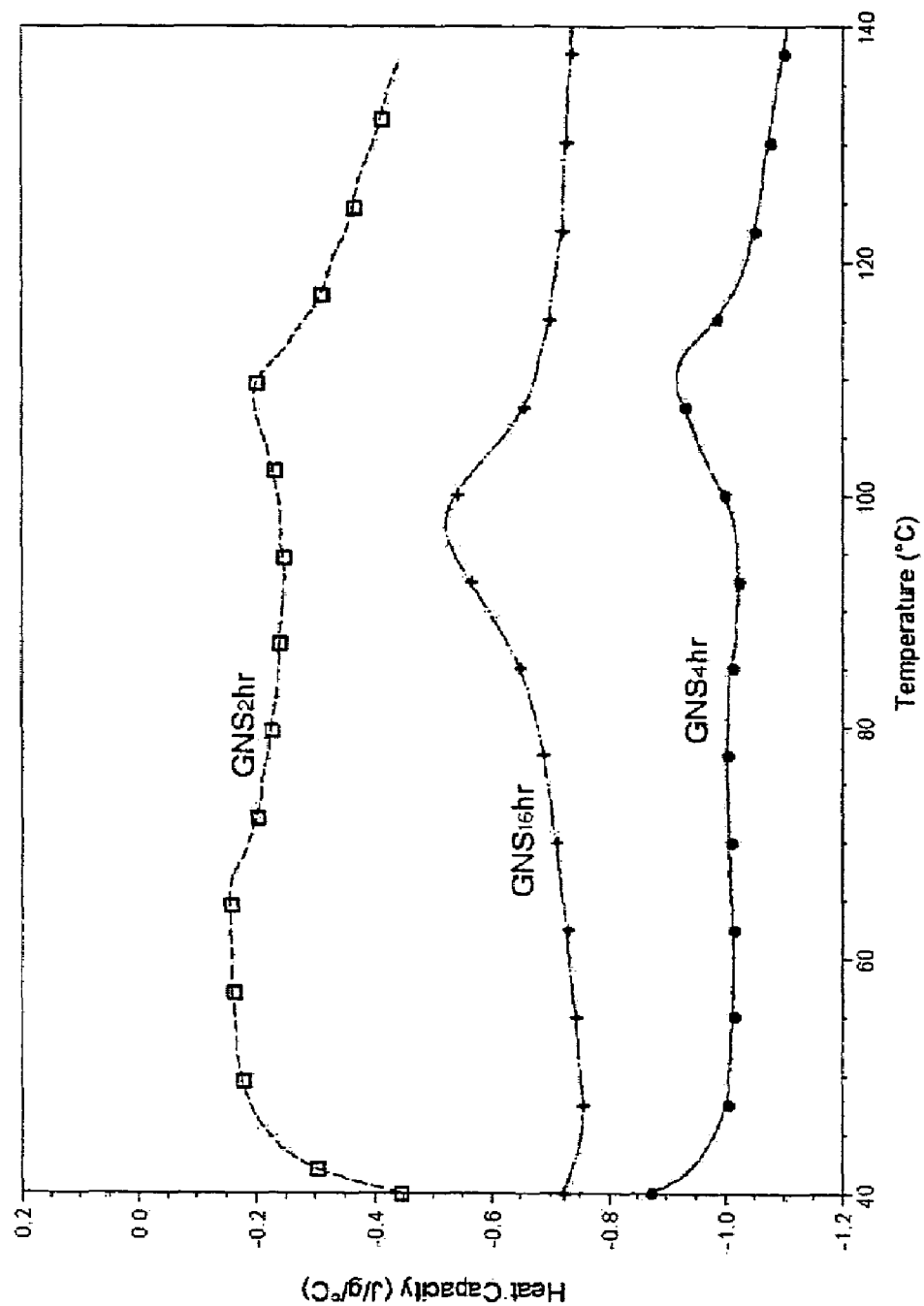
FIG. 10 illustrates the results of differential scanning calorimetry of gelatinized rice flour that was not stored before being incubated with pullulanase for either 2 hr (GNS2 hr), 4 hr (GNS4 hr), or 16 hr (GNS16 hr).
Figure 11:
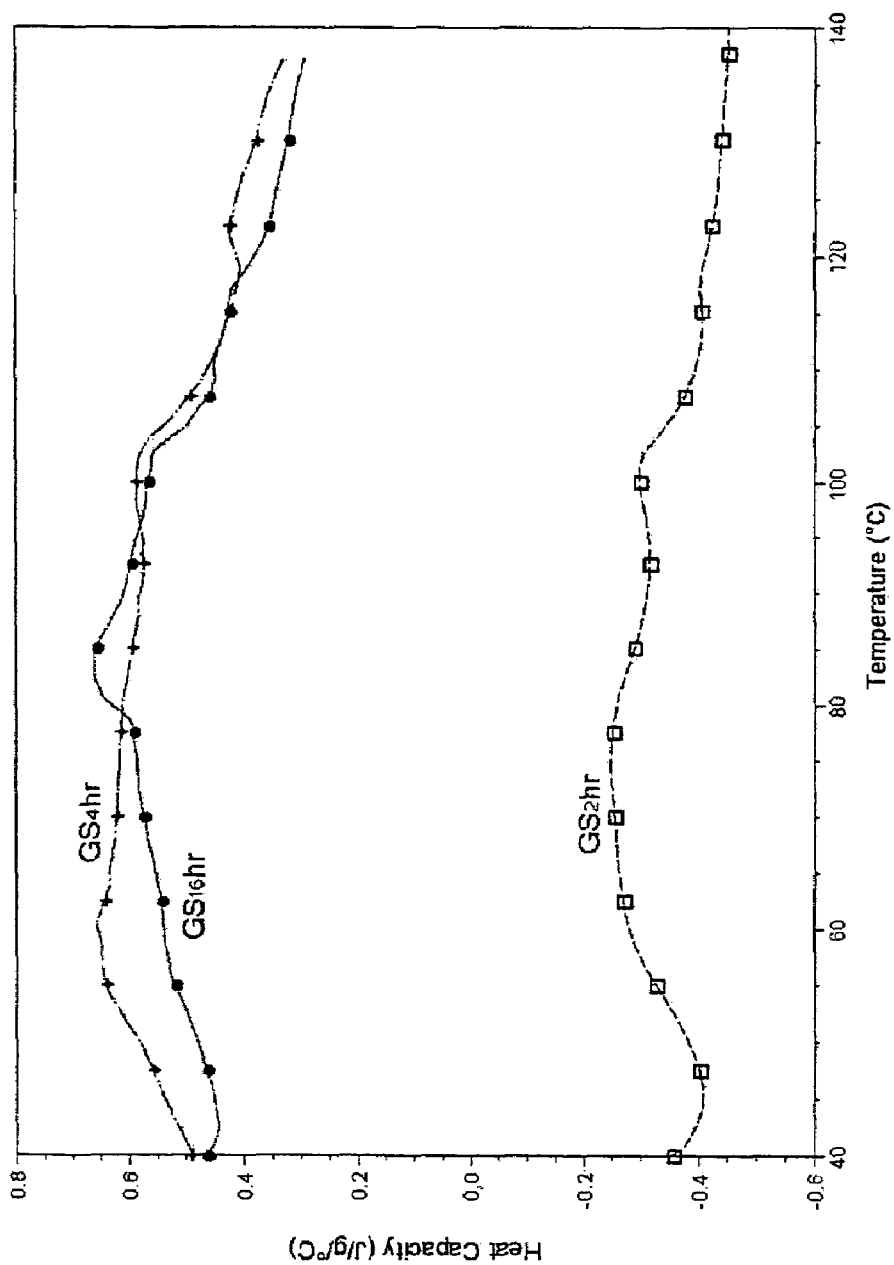
FIG. 11 illustrates the results of differential scanning calorimetry of gelatinized rice flour that was stored overnight before being incubated with pullulanase for either 2 hr (GS2 hr), 4 hr (GS4 hr), or 16 hr (GS16 hr).

[1]$T_O$, $T_P$, $T_C$ = onset, peak and completion temperatures, respectively; ΔH = enthalpy; ND = non-detectable.
[2]Means with different letters within each column are significantly different at $p \leq 0.05$. The values are an average of 2 to 4 measures.
[3]Units: Temperature (° C.), Enthalpy (J/g, dry matter); Heating Rate = 5° C./min For the resistant starch peak, no significant difference were found in the commercial control, untreated rice flour and all the treated samples for peak onset, peak and completion temperature. For the NGNS4 hr, GNS2 hr, and GNS4 hr treated samples, no resistant starch peak was detected (FIGS. 9, 10, and 11). The resistant starch peak in the commercial control, CrystaLean® (100 to 130° C.), appeared to be two peaks overlapping each other so that the start and end points of the peaks were not distinct (FIG. 8). According to the DSC results, the NGNS2 hr and 16 hr, GNS16 hr, and GS treated samples contained resistant starch (FIGS. 8, 9, 10, and 11; Table 14).

EXAMPLE 17

Effects of α-Amylase Treatment on the Heating Profile of Rice Flour

On the α-amylase-treated samples, the NGNS2 hr and 4 hr, GNS2 hr, and GS4 hr samples did not have a gelatinization peak. The onset, peak and completion temperatures of the NGNS16 hr, GNS4 hr and 16 hr, and GS2 hr and 16 hr treated samples were not significantly different from the untreated rice flour in gelatinization temperatures and peak enthalpies (Table 15, heating profile graphs not shown).

The onset temperature range for the amylose-lipid complex peak was 82.2 to 104° C. (Table 15). The peak onset temperature for NGNS4 hr was approximately 20° C. lower than the GNS16 hr, GS4 hr and GS16 hr treated samples, a significant difference ($p \leq 0.05$). No significant differences were found in enthalpies for all the treated samples and the untreated rice flour (Table 15).

The resistant starch peak for the commercial control had an enthalpy of 3.69 J/g. The highest peak enthalpies were observed in the GS2 hr and GS4 hr treated samples, 125 and 108 J/g, respectively (Table 15). They were significantly higher in peak onset temperature than the commercial control ($p \leq 0.05$). Incubation time within the NGNS treatments did not produce a significant difference in peak enthalpy (Table 15). No significant differences were detected in the treated samples, commercial control, and untreated rice flour in the resistant starch peak temperature.

Based on the DSC analysis, 3 α-amylase-treated samples (GNS2 hr and 16 hr, and GS16 hr) did not contain resistant starch. However, gelatinization type and incubation period did not effect peak onset, peak, and completion temperatures.

treated samples were significantly lower than that of the untreated rice flour (2.85 J/g) ($p \leq 0.05$).

For the GS2 hr treated sample, the amylose-lipid complex peak onset temperature was significantly lower ($p \leq 0.05$) than that of the untreated rice flour. The peak enthalpy for the GS2 hr (1.84 J/g) treated sample was significantly higher than the NGNS2 hr and 4 hr treated samples (0.15 J/g), and untreated rice flour (0.18 J/g) ($p \leq 0.05$).

Neither the NGNS16 hr nor all GNS treatments resulted in a resistant starch peak. NGNS2 hr and 4 hr and all the GS

TABLE 15

Effects of Gelatinization/Storage and Incubation Duration on Thermal Characteristics of α-Amylase Treated Rice Flour[1,2,3]

| Sample | Treatment | First Transition (Gelatinization) | | | | Second Transition (Amylose-lipid complex) | | | | Third Transition (Resistant Starch) | | | |
|---|---|---|---|---|---|---|---|---|---|---|---|---|---|
| | | $T_0$ | $T_P$ | $T_C$ | ΔH | $T_0$ | $T_P$ | $T_C$ | ΔH | $T_0$ | $T_P$ | $T_C$ | ΔH |
| Control | — | ND | ND | ND | ND | ND | ND | ND | ND | 101b | 119a | 133a | 3.69a |
| Rice Flour | — | 70.9a | 77.8a | 92.0a | 2.85a | 94.2ab | 100ab | 106a | 0.18a | 118ab | 119a | 128a | 0.17a |
| α-Amylase | NGNS2hr | ND | ND | ND | ND | 88.3ab | 94.5ab | 108a | 4.06a | 108ab | 112a | 118a | 0.86a |
| | NGNS4hr | ND | ND | ND | ND | 82.2b | 85.2b | 94.5a | 0.26a | 102b | 111a | 129a | 0.191a |
| | NGNS16hr | 71.0a | 75.0a | 86.0a | 1.48a | 96.3ab | 104ab | 114a | 1.06a | 108ab | 114a | 120a | 0.14a |
| | GNS2hr | ND | ND | ND | ND | 99.8ab | 109ab | 126a | 1.82a | ND | ND | ND | ND |
| | GNS4hr | 58.6a | 66.0a | 78.1a | 0.121a | 90.0ab | 97.0ab | 88.4a | 26.4a | 106ab | 119a | 128a | 2.02a |
| | GNS16hr | 59.7a | 83.1a | 84.9a | 0.664a | 104a | 110a | 126a | 0.89a | ND | ND | ND | ND |
| | GS2hr | 67.8a | 71.0a | 97.4a | 1.84a | 98.9ab | 105ab | 114a | 0.46a | 122a | 126a | 134a | 125a |
| | GS4hr | ND | ND | ND | ND | 101a | 110a | 120a | 2.52a | 120a | 126a | 134a | 108a |
| | GS16hr | 64.6a | 67.4a | 77.1a | 0.226a | 100a | 108ab | 121a | 1.55a | ND | ND | ND | ND |

[1]$T_0, T_P, T_C$ = onset, peak and completion temperatures, respectively; ΔH = enthalpy; ND = non-detectable.
[2]Means with different letters within each column are significantly different at $p \leq 0.05$. The values are an average of 2 to 4 measurements.
[3]Units: Temperature (° C.), Enthalpy (J/g, dry matter); Heating Rate = 5° C./min

EXAMPLE 18

Effects of α-Amylase-Pullulanase Treatment on the Heating Profile of Rice Flour

For samples treated with both α-amylase and pullulanase, a gelatinization peak for the NGNS16 hr, GNS4 hr and 16 hr, and GS2 hr and 16 hr samples was not detected. No significant differences were seen in the gelatinization peak onset, peak, and completion temperatures between the NGNS2 hr and 4 hr, GNS2 hr and GS4 hr treated samples and the untreated rice flour (Table 16, no heating profile graphs shown). The peak enthalpies for the GNS2 hr (0.144 J/g) and GS4 hr (0.602 J/g) treatments were similar to both the commercial control and untreated rice flour in peak onset, peak and completion temperatures, and peak enthalpies.

Incubation time did not have a significant effect on the gelatinization type (Table 16). The enzyme treatments did not produce a significant amount of resistant starch as shown in Table 4; however, the small amount present in the samples was detected by DSC. The non-significant differences between the wide ranges of temperature within each variable, peak onset, peak, and completion temperatures were due to inconsistent results during analysis.

TABLE 16

Effects of Gelatinization/Storage and Incubation Duration on Thermal Characteristics of α-Amylase-Pullulanase Treated Rice Flour[1,2,3]

| Sample | Treatment | First Transition (Gelatinization) | | | | Second Transition (Amylose-lipid complex) | | | | Third Transition (Resistant Starch) | | | |
|---|---|---|---|---|---|---|---|---|---|---|---|---|---|
| | | $T_0$ | $T_P$ | $T_C$ | ΔH | $T_0$ | $T_P$ | $T_C$ | ΔH | $T_0$ | $T_P$ | $T_C$ | ΔH |
| Control | — | ND | ND | ND | ND | ND | ND | ND | ND | 101a | 119a | 133a | 3.69a |
| Rice Flour | — | 70.9a | 77.8a | 92.0a | 2.85a | 94.2a | 100ab | 106a | 0.184a | 118a | 119a | 128a | 0.17a |
| α-Amylase-Pullulanase | NGNS2hr | 71.7a | 78.2a | 93.6a | 3.04a | 95.5a | 101ab | 108a | 0.157a | 115a | 119a | 126a | 0.09a |
| | NGNS4hr | 73.3a | 77.8a | 91.6a | 3.18a | 92.2a | 95.7ab | 102a | 0.157a | 105a | 111a | 121a | 0.56a |
| | NGNS16hr | ND | ND | ND | ND | 97.1a | 106a | 118a | 1.23ab | ND | ND | ND | ND |
| | GNS2hr | 57.7a | 64.2a | 77.8a | 0.144b | 97.7a | 106a | 119a | 1.24ab | ND | ND | ND | ND |
| | GNS4hr | ND | ND | ND | ND | 100a | 109a | 123a | 1.43ab | ND | ND | ND | ND |
| | GNS16hr | ND | ND | ND | ND | 97.6a | 105a | 119a | 1.05ab | ND | ND | ND | ND |
| | GS2hr | ND | ND | ND | ND | 73.9b | 86.8b | 101a | 1.84a | 109a | 115a | 124a | 117a |

TABLE 16-continued

Effects of Gelatinization/Storage and Incubation Duration on
Thermal Characteristics of α-Amylase-Pullulanase Treated Rice Flour[1,2,3]

| Sample | Treatment | First Transition (Gelatinization) | | | | Second Transition (Amylose-lipid complex) | | | | Third Transition (Resistant Starch) | | | |
|---|---|---|---|---|---|---|---|---|---|---|---|---|---|
| | | $T_0$ | $T_p$ | $T_C$ | ΔH | $T_0$ | $T_p$ | $T_C$ | ΔH | $T_0$ | $T_p$ | $T_C$ | ΔH |
| | GS4hr | 58.7a | 67.9a | 79.7a | 0.602b | 99.5a | 104a | 111a | 1.21ab | 106a | 117a | 123a | 1.52a |
| | GS16hr | ND | ND | ND | ND | 94.9a | 102ab | 113a | 1.41ab | 113a | 122a | 133a | 53.8a |

[1]$T_0$, $T_p$, $T_C$ = onset, peak and completion temperatures, respectively; ΔH = enthalpy; ND = non-detectable.
[2]Means with different letters within each column are significantly different at p ≦ 0.05. The values are an average of 2 to 4 measures.
[3]Units: Temperature (° C.), Enthalpy (J/g, dry matter); Heating Rate = 5° C./min

EXAMPLE 19

Effects of Pullulanase Treatment on Heating Profile of Rice Starch

Figure 12:
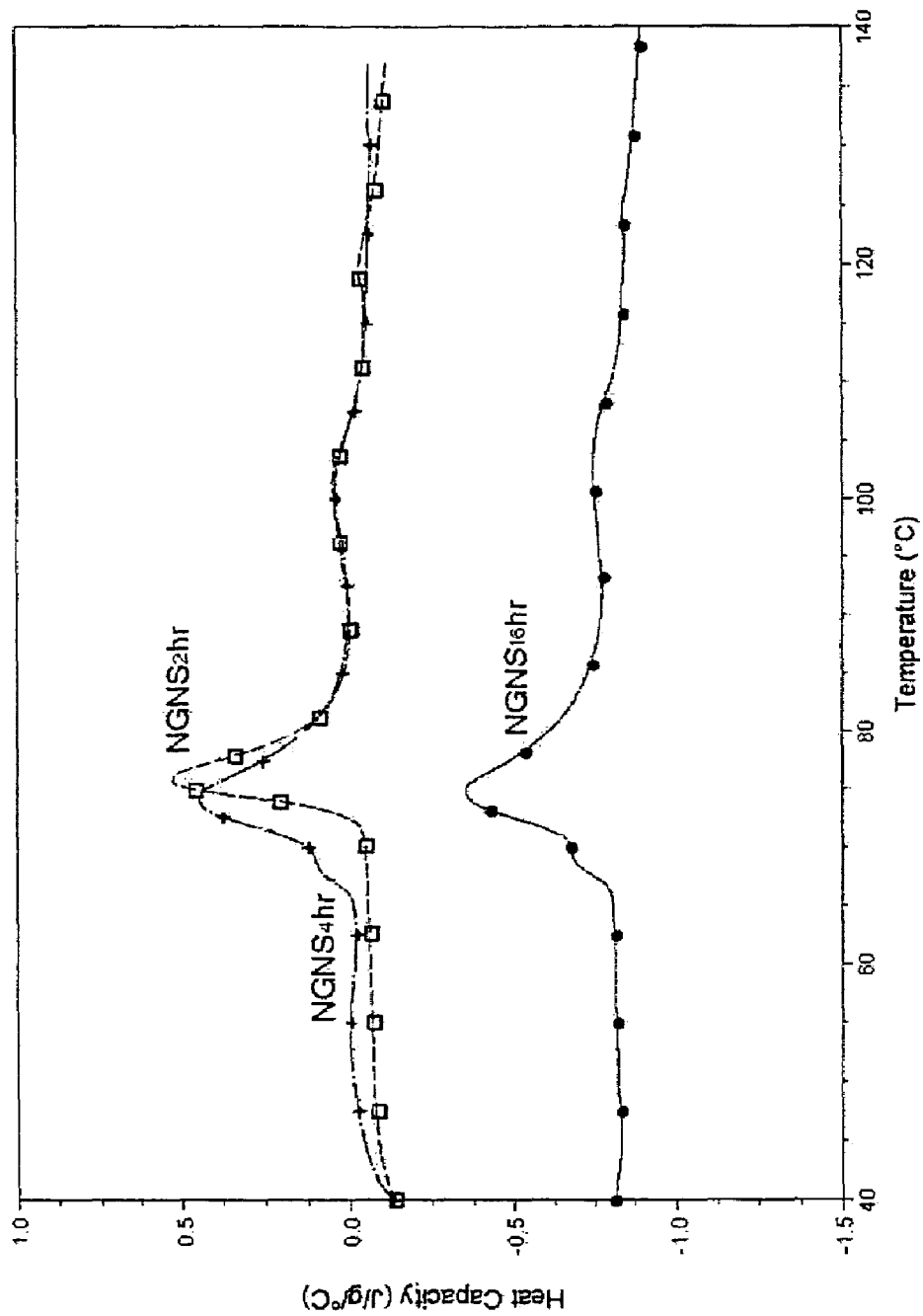
FIG. 12 illustrates the results of differential scanning calorimetry of non-gelatinized rice starch that was not stored before being incubated with the enzyme pullulanase for either 2 hr (NGNS2 hr), 4 hr (NGNS4 hr), or 16 hr (NGNS16 hr).

For the samples incubated with pullulanase, the NGNS-treated samples had gelatinization characteristics similar to the untreated rice starch (Table 17; FIGS. 8 and 12). The peak enthalpy was also not different from the untreated rice starch. The NGNS treated samples were not significantly different from each other. The GNS-treated samples did not show a gelatinization peak (Table 17; heating profile graphs not shown), which was expected since the samples had been gelatinized at 95° C. prior to enzyme treatment. However, the GS-treated samples had an unexpected gelatinization peak and were not significantly different from the untreated rice starch (Table 17). The enthalpies of the GS2 hr and 16 hr treated samples, however, were significantly lower (p≦0.05) than that of the untreated rice starch and the NGNS treated samples. The peak onset range was 62.8 to 73.1° C., peak range was 74.2 to 81.3° C., and completion range was 85.5 to 96.7° C.

No significant difference was found in amylose-lipid complex peak onset, peak, and completion temperatures, and enthalpies in the treated samples and the untreated rice starch (Table 17). The peak onset range was 69.2 to 99.7° C., peak range was 73.6 to 121° C., and completion range was 79.4 to 121° C.

A resistant starch peak was not detected in the NGNS16 hr treated sample. No significant differences were found in peak onset and peak temperatures between the other treated rice starch samples, untreated rice starch, and commercial control (p>0.05). The peak completion temperature in GS16 hr was significantly higher (12° C.) than the untreated rice starch (p≦0.05). The enthalpies ranged from 0.00835 to 0.3 J/g (Table 17). The peak onset range was 96.8 to 120° C., peak range was 120 to 125° C., and completion range was 125 to 133° C.

TABLE 17

Effects of Gelatinization/Storage and Incubation Duration on
Thermal Characteristics of Pullulanase Treated Rice Starch[1,2,3]

| Sample | Treatment | First Transition (Gelatinization) | | | | Second Transition (Amylose-lipid complex) | | | | Third Transition (Resistant Starch) | | | |
|---|---|---|---|---|---|---|---|---|---|---|---|---|---|
| | | $T_0$ | $T_p$ | $T_C$ | ΔH | $T_0$ | $T_p$ | $T_C$ | ΔH | $T_0$ | $T_p$ | $T_C$ | ΔH |
| Control | — | ND | ND | ND | ND | ND | ND | ND | ND | 101a | 119a | 132a | 3.6b |
| Rice Starch | — | 68.8ab | 73.3a | 83.6b | 2.99ab | 90.0a | 97.4a | 116a | 0.45a | 112a | 116a | 121b | 0.12b |
| Pullulanase | NGNS2hr | 70.8ab | 75.3a | 89.3ab | 3.96a | 94.2a | 103a | 113a | 0.92a | 96.8a | 124a | 127ab | 0.11b |
| | NGNS4hr | 69.7ab | 74.8a | 88.6ab | 3.56a | 69.2a | 73.6a | 79.4a | 0.32a | 117a | 120a | 131ab | 0.00835a |
| | NGNS16hr | 70.3ab | 75.3a | 88.1ab | 3.82a | 93.6a | 103a | 111a | 0.49a | ND | ND | ND | ND |
| | GNS2hr | ND | ND | ND | ND | 90.2a | 104a | 115a | 2.05a | 118a | 121a | 129ab | 0.3b |
| | GNS4hr | ND | ND | ND | ND | 88.1a | 105a | 116a | 2.17a | 119a | 122a | 130ab | 0.32b |
| | GNS16hr | ND | ND | ND | ND | ND | ND | ND | ND | 120a | 122a | 127ab | 0.04b |
| | GS2hr | 73.1a | 81.3a | 92.8ab | 0.212c | 97.0a | 104a | 112a | 0.32a | 119a | 122a | 126ab | 0.05b |
| | GS4hr | 62.8b | 79.1a | 96.7a | 1.23bc | 99.0a | 105a | 113a | 0.32a | 120a | 122a | 125ab | 0.02b |
| | GS16hr | 63.9b | 74.2a | 85.5ab | 0.397c | 99.7a | 112a | 121a | 179a | 119a | 125a | 133a | 0.18b |

[1]$T_0$, $T_p$, $T_C$ = onset, peak and completion temperatures, respectively; ΔH = enthalpy; ND = non-detectable.
[2]Means with different letters within each column are significantly different at p ≦ 0.05. The values are an average of 2 to 4 measures.
[3]Units: Temperature (° C.), Enthalpy (J/g, dry matter); Heating Rate = 5° C./min

EXAMPLE 20

Effects of α-Amylase Treatment on the Heating Profile of Rice Starch

For α-amylase-treated rice starch, the gelatinization peak onset range was 56.3 to 76.6° C., peak range was 68.2 to 92.1° C., and completion range was 86.4 to 106° C. (Table 18). No differences were found between any sample and the untreated rice starch in gelatinization temperatures and enthalpies, except GS2 hr had significantly greater peak and completion temperatures. The GNS4 hr and 16 hr, and GS4 hr-treated samples did not have a gelatinization peak. The enthalpy of peaks ranged from 0.43 to 3.29 J/g, and the NGNS2 hr-treated sample had the highest enthalpy, 4.03 J/g.

For the amylose-lipid complex, the peak onset range was 91.8 to 105° C., peak range was 103 to 122° C., and completion range was 92.3 to 139° C. The GNS4 hr-treated sample had the lowest onset and peak temperatures, and GS16 hr sample had the highest. The non-significant differences between the onset, peak and completion temperatures were due to inconsistent data from DSC analysis. Different treatments caused the peak onset and peak temperatures to vary slightly (Table 18; heat profile graphs not shown). No significant difference was seen in the completion temperatures and peak enthalpies. The peak enthalpies ranged from 0.23 to 4.45 J/g; the lowest was the GNS4 hr-treated sample, and the highest was the NGNS 16 hr sample.

The NGNS2 hr, GNS2 hr and 4 hr, and GS16 hr-treated samples did not have a resistant starch peak. The GS4 hr-treated sample had the lowest temperature for peak onset (111° C.), peak (119° C.), and completion (126° C.). The highest temperature for peak onset was 124° C. in NGNS16 hr sample, for peak was 125° C. in NGNS16 hr sample, and for completion was 136.0° C. in GNS16 hr sample. The non-significant differences between the wide temperature ranges were due to inconsistent data from DSC analysis. The treatment with the highest enthalpy, 7.42 J/g, was NGNS16 hr, while GS4 hr had the lowest enthalpy, 0.343 J/g.

hr-treated sample had the highest enthalpy at 4.77 J/g, while the NGNS16 hr-treated sample had the lowest, 0.146 J/g. The enthalpies ranged from 0.146 to 4.77 J/g. The GNS2 hr and 16 hr-treated samples had a gelatinization peak during DSC analysis, probably indicating that the gelatinization prior to enzyme incubation was incomplete. The peak onset range was 60.8 to 74.5° C., peak range was 72.9 to 78.1° C., and completion range was 81.8 to 96.5° C. (Table 19) The NGNS16 hr and GNS2 hr-treated samples were significantly lower than the NGNS2 hr and 4 hr treated samples and the untreated rice starch in peak onset temperature ($p \leq 0.05$). No significant difference was found in the peak or peak completion temperature for NGNS, GNS2 hr and 16 hr treatments, and the untreated rice starch. The NGNS16 hr treated sample had a lower peak enthalpy than the NGNS4 hr treated sample ($p \leq 0.05$).

For the GNS4 hr-treated sample, no amylose-lipid complex peak was detected (Table 19). The remaining treatments, NGNS (all), GNS2 hr and 16 hr, and GS (all), were not significantly different from the untreated rice starch for presence of amylose-lipid complex. The enthalpies for all the treated samples and untreated rice starch ranged from 0.177 to 12.0 J/g, but were not significantly different from each other. The peak onset range was 84.3 to 105° C., peak range was 93.5 to 114° C., and completion range was 105 to 122° C.

TABLE 18

Effects of Gelatinization/Storage and Incubation Duration on Thermal Characteristics of α-Amylase Treated Rice Starch[1,2,3]

| Sample | Treatment | First Transition (Gelatinization) | | | | Second Transition (Amylose-lipid complex) | | | | Third Transition (Resistant Starch) | | | |
|---|---|---|---|---|---|---|---|---|---|---|---|---|---|
| | | $T_O$ | $T_P$ | $T_C$ | ΔH | $T_O$ | $T_P$ | $T_C$ | ΔH | $T_O$ | $T_P$ | $T_C$ | ΔH |
| Control | — | ND | ND | ND | ND | ND | ND | ND | ND | 101b | 119a | 133a | 3.69a |
| Rice Starch | — | 68.8a | 73.3b | 83.6b | 2.99a | 89.8a | 97.4b | 116a | 0.450a | 112ab | 116a | 121a | 0.124a |
| α-Amylase | NGNS2hr | 70.6ab | 75.7b | 91.7ab | 4.03a | 96.3a | 104ab | 116a | 0.360a | ND | ND | ND | ND |
| | NGNS4hr | 74.9a | 78.2b | 90.7ab | 3.29a | 100a | 104ab | 111a | 0.229a | 116ab | 119a | 131a | 1.04a |
| | NGNS16hr | 76.6a | 79.8ab | 92.6ab | 2.68a | 100a | 106ab | 92.3a | 4.45a | 124a | 125a | 134a | 7.42a |
| | GNS2hr | 56.3b | 68.2b | 86.6b | 0.434a | 95.9a | 110ab | 126a | 0.39a | ND | ND | ND | ND |
| | GNS4hr | ND | ND | ND | ND | 100a | 111ab | 122a | 0.221a | ND | ND | ND | ND |
| | GNS16hr | ND | ND | ND | ND | 91.8a | 105ab | 116a | 0.669a | 114ab | 121a | 136a | 0.551a |
| | GS2hr | 76.7a | 92.1a | 106a | 2.14a | 98.0a | 103ab | 113a | 1.64a | 113ab | 120a | 130a | 0.3490 |
| | GS4hr | ND | ND | ND | ND | ND | ND | ND | ND | 111ab | 119a | 126a | 0.343a |
| | GS16hr | 64.0ab | 73.3b | 86.4b | 0.597a | 105a | 122a | 139a | 3.20a | ND | ND | ND | ND |

[1] $T_O$, $T_P$, $T_C$ = onset, peak and completion temperatures, respectively; ΔH = enthalpy; ND = non-detectable.
[2] Means with different letters within each column are significantly different at $p \leq 0.05$. The values are an average of 2 to 4 measures.
[3] Units: Temperature (° C.), Enthalpy (J/g, dry matter); Heating Rate = 5° C./min

EXAMPLE 21

Effects of α-Amylase-Pullulanase Treatment on the Heating Profile of Rice Starch For the α-amylase-pullulanase enzyme treatments, GNS4 hr, GS2 hr, 4 hr and 16 hr did not have a gelatinization peak (Table 19; heating profile graphs not shown). The NGNS4

The resistant starch peak temperatures for the α-amylase-pullulanase treated rice starch were not significantly different from the commercial control or from the untreated rice starch. The peak enthalpies ranged from 0.071 to 10.2 J/g. The lowest peak enthalpy was 0.071 J/g for the NGNS2 hr sample (Table 19), and the highest for GNS16 hr, 10.2 J/g. The peak onset range was 109 to 120° C., peak range was 115 to 126° C., and completion range was 122 to 137° C.

TABLE 19

Effects of Gelatinization/Storage and Incubation Duration on
Thermal Characteristics of α-Amylase-Pullulanase Treated Rice Starch[1,2,3]

| Sample | Treatment | First Transition (Gelatinization) | | | | Second Transition (Amylose-lipid complex) | | | | Third Transition (Resistant Starch) | | | |
|---|---|---|---|---|---|---|---|---|---|---|---|---|---|
| | | $T_0$ | $T_p$ | $T_C$ | ΔH | $T_0$ | $T_p$ | $T_C$ | ΔH | $T_0$ | $T_p$ | $T_C$ | ΔH |
| Control | — | ND | ND | ND | ND | ND | ND | ND | ND | 101a | 119a | 133a | 3.69a |
| Rice Starch | — | 68.8bc | 73.3a | 83.6a | 2.99ab | 89.8a | 97.4a | 116a | 0.45a | 112a | 116a | 121a | 0.124a |
| α-Amylase-Pullulanase | NGNS2hr | 72.5a | 76.9a | 92.8a | 3.47a | 98.2a | 102a | 108a | 0.178a | 83.8a | 84.7a | 87.8a | 0.071a |
| | NGNS4hr | 74.5a | 77.3a | 90.8a | 4.77a | 97.0a | 100a | 106a | 2.22a | 114a | 116a | 122a | 0.808a |
| | NGNS16hr | 62.6d | 72.9a | 81.8a | 0.146b | 101a | 103a | 113a | 0.177a | 120a | 122a | 130a | 0.095a |
| | GNS2hr | 60.8d | 78.1a | 96.5a | 1.92ab | 105a | 114a | 122a | 0.143a | ND | ND | ND | ND |
| | GNS4hr | ND | ND | ND | ND | ND | ND | ND | ND | 114a | 126a | 137a | 0.31a |
| | GNS16hr | 63.7cd | 74.5a | 85.2a | 0.727b | 98.2a | 106a | 113a | 0.189a | 117a | 123a | 131a | 0.369a |
| | GS2hr | ND | ND | ND | ND | 84.3a | 93.5a | 105a | 1.09a | 117a | 123a | 131a | 0.37a |
| | GS4hr | ND | ND | ND | ND | 95.1a | 98.5a | 112a | 12.0a | 114a | 122a | 133a | 0.999a |
| | GS16hr | ND | ND | ND | ND | 88.6a | 97.7a | 108a | 6.38a | 109a | 115a | 125a | 10.2a |

[1]$T_0$, $T_p$, $T_C$ = onset, peak and completion temperatures, respectively; ΔH = enthalpy; ND = non-detectable.
[2]Means with different letters within each column are significantly different at $p \leq 0.05$. The values are an average of 2 to 4 measures.
[3]Units: Temperature (° C.), Enthalpy (J/g, dry matter); Heating Rate = 5° C./min

EXAMPLE 22

Stability of Resistant Starch Peaks

When a resistant starch peak was identified in DSC from the treated rice flour and starch samples, the same sample was reheated to 140° C. to examine the heat stability of resistant starch. The 27 samples found to have resistant starch that was heat stable are presented in Table 20.

Five rice flour treatments increased in peak enthalpy during reheating: three pullulanase samples, GNS2 hr, GS2 hr and 4 hr; and two α-amylase-pullulanase samples, NGNS2 hr and GS4 hr. In the rice starch samples, GS2 hr (pullulanase) was the only sample that indicated an increase in peak enthalpy during reheating. The peak enthalpies of GS16 h (pullulanase, rice starch) and GS4 hr and 16 hr (α-amylase-pullulanase, rice starch) were significantly reduced to about 3% after reheating. No clear pattern was detected on the influence of gelatinization, incubation time, and type of enzyme on the heat stability of resistant starch.

For both rice flour and starch, all three enzyme treatments produced resistant starch according to the DSC analysis. Pullulanase treatments produced the most samples that had heat stable resistant starch, followed by α-amylase-pullulanase, and then α-amylase. This trend was observed in both rice flour and starch.

The resistant starch formed from pullulanase treated starch consisted of both linear amylose chains cleaved from amylopectin and original amylose chains. The resistant starch present in the α-amylase and α-amylase-pullulanase treatments, however, probably had fewer and shorter linear amylose chains due to the random cleaving by α-amylase. When pullulanase debranched the starch molecules in the α-amylase-pullulanase treatment, the linear chains became highly accessible to the α-amylase, and greater amount of degradation to the starch molecules occurred.

TABLE 20

Enthalpy of Heat-stable Resistant Starch Peaks

| Sample | Treatment | Original ΔH (J/g) | Final H (J/g) | % Remaining |
|---|---|---|---|---|
| Rice Starch | | | | |
| Pullulanase | NGNS2 hr | 2.11 | 0.745 | 35.3 |
| | NGNS4 hr | 0.778 | 0.764 | 98.2 |
| | GNS2 hr | 2.73 | 2.05 | 75.1 |
| | GSN4 hr | 2.48 | 2.26 | 91.1 |
| | GNS16 hr | 8.81 | 5.6 | 63.6 |
| | GS2 hr | 0.349 | 0.969 | 278 |
| | GS16 hr | 569 | 12.0 | 2.1 |
| Amylase-pullulanase | NGNS4 hr | 8.88 | 1.36 | 15.3 |
| | GS2 hr | 2.86 | 0.62 | 21.7 |
| | GS4 hr | 65.19 | 2.17 | 3.3 |
| | GS16 hr | 11.51 | 0.256 | 2.2 |
| Amylase | NGNS4 hr | 3.84 | 2.11 | 54.9 |
| | GS2 hr | 1.79 | 0.56 | 31.3 |
| | GS16 hr | 1.65 | 1.6 | 97.0 |
| Flour | | | | |
| Pullulanase | NGNS2 hr | 4.73 | 2.7 | 57.1 |
| | NGNS4 hr | 4.31 | 0.893 | 20.7 |
| | GNS2 hr | 0.971 | 1.18 | 122 |
| | GNS16 hr | 8.17 | 5.05 | 61.8 |
| | GS2 hr | 0.406 | 1.78 | 438 |
| | GS4 hr | 0.526 | 1.67 | 317 |
| | GS16 hr | 3.89 | 2.42 | 62.1 |
| Amylase-pullulanase | NGNS2 hr | 0.225 | 0.329 | 146 |
| | GS2 hr | 351 | 72.9 | 20.8 |
| | GS4 hr | 3.35 | 8.06 | 241 |
| | GS16 hr | 152 | 49.9 | 32.8 |
| Amylase | GS2 hr | 373 | 69.9 | 18.7 |
| | GS4 hr | 213 | 127 | 59.6 |

Of all the non-gelatinized (NGNS) treatments on rice flour and rice starch, only three samples did not have a gelatinization peak: NGNS16 hr (α-amylase-pullulanase, rice flour), and NGNS2 hr and 4 hr (α-amylase, rice flour). Although some of the GNS and GS samples had gelatinization peaks when analyzed with DSC, this was probably due to incomplete gelatinization during sample preparation Only three rice starch samples did not have a second transition peak: GNS16 hr (pullulanase), GNS4 hr (α-amylasepullulanase), and GS4 hr (α-amylase). The highest peak enthalpy was 179 J/g in a single GS16 hr treated sample (pullulanase, rice starch). The rest of the treated samples (rice flour and starch) had enthalpies between 0.5 and 2 J/g.

Resistant starch was detected in most of the enzyme treated samples. The enzyme combinations, incubation time, and gelatinization type did not cause a significant difference in the thermal properties of the resistant starch formed from rice flour and rice starch. The resistant starch peak was heat stable. Heat stability is important because then resistant rice starch can be incorporated into a wider variety of food products, such as frozen dinners that require a second heating before consumption.

Enzyme treatments on rice starch and flour produced resistant starch (RS) yields on a wide scale. The RS yields were dependent on the source of starch, gelatinization type, incubation period, and enzyme combination. The rice starch produced a higher RS yield than rice flour for most of the treatments. The non-gelatinized (NGNS) treatments yielded the highest RS content for both rice starch and rice flour. In rice starch, the NGNS (pullulanase) treated samples had a yield of 40 to 61% RS (based on dry weight). There was no discernable trend in incubation time. Some 16 hr treatments had significantly higher yields while others had lower yields. For enzymatic treatments, pullulanase produced the best resistant starch yields in both rice starch and flour. The lower yields seen in α-amylase-pullulanase and α-amylase treatments were attributed to the random cleaving effects of α-amylase, degrading the amylose present.

Gelatinization, regardless of enzyme treatment, deteriorated or minimized the pasting characteristics of the rice flour and starch, as analyzed using rapid visco amylograph (RVA). The non-gelatinized-no-overnight-storage (pullulanase) samples had the best pasting characteristics among all the treatments, probably due to the milder temperature (55° C.) of incubation and the pattern of enzyme cleavage on starch. The non-gelatinized, pullulanase samples were also the most similar in pasting characteristics to the untreated rice flour and starch.

DSC analysis of the samples was difficult to interpret due to large variations in the data, and because some of the pre-gelatinized samples indicated the presence of gelatinization peaks, probably indicating an incomplete initial gelatinization process. Amylose-lipid complex and resistant starch were detected in both rice starch and rice flour samples. The samples with resistant starch peaks were reheated to test the heat stability of the resistant starch present. A number of samples from both rice flour and rice starch tested positive for resistant starch heat stability. Three samples (GS16 hr (pullulanase, rice starch), and GS4 hr and 16 hr α-amylase-pullulanase, rice starch)) retained a resistant starch peak during reheating; however the peak enthalpies were reduced to about 3% of the initial peak enthalpy.

Non-gelatinized rice starch treated with pullulanase for 2 to 4 hours yielded the highest amounts of resistant starch levels that retained its pasting characteristics. This resistant rice starch may be used as a value-added food ingredient. CrystaLean®, the commercial resistant starch made from corn, is currently used in diabetic candy bars as a bulking agent. The rice resistant starch as produced by pullulanase treatment on non-gelatinized samples may have wider range of use as the rice resistant starch retained its pasting properties while CrystaLean® did not. This specific treatment produced a starch with same pasting characteristics as untreated rice starch, but with 8 to 12 times more resistant starch (fiber). The resistant starch was also heat resistant, as a peak was detected during reheating. This was significant because this resistant rice starch could be used in food products that are heated, and have a high viscosity. It could also be incorporated into frozen dinners where reheating is a prerequisite. Rice is also hypoallergenic due to its low protein content, and would therefore be less likely to cause food allergies in consumers. Moreover, resistant starch was formed from starch with less than 30% amylose and without heating the starch above 60° C.

As used in the specification and the claims, the term "native starch" means a starch that has not been pre-treated, including starch that has not been heated to cause gelatinization or treated chemically or enzymatically to cause hydrolysis.

The complete disclosures of all references cited in this application are hereby incorporated by reference. Also, incorporated by reference is the complete disclosure of the following documents: Siow Ying Tan, "Resistant Rice Starch Development," A thesis submitted to the Department of Food Science, Louisiana State University, August, 2003; S. Y. Tan and J. M. King, "Enzymatic treatment to form resistant rice starch," An abstract for the 2003 Annual Meeting of the Institute of Food Technologists, published online March 2003; and S. Y. Tan and J. M. King, "Enzymatic Treatment to form Resistant Rice Starch," a poster presented on Jul. 14, 2003, at the 2003 Annual Meeting of the Institute of Food Technologists, Chicago, Ill. In the event of an otherwise irreconcilable conflict, however, the present specification shall control.kj n

We claim:

1. An insoluble resistant starch product produced from a native ungelatinized, unhydrolyzed insoluble starch, wherein said product exhibits a pasting temperature and a peak viscosity that are within 25% of that exhibited by the native starch, wherein said product contains a higher percentage of starch molecules that are resistant to alpha-amylase digestion as compared to the native starch, wherein said product displays a resistant starch temperature peak from about 116° C. to about 125° C. in a heating profile as measured by differential scanning calorimetry, wherein said product has from about three-fold to about twelve-fold increase in the percentage of starch molecules that are resistant to alpha-amylase digestion as compared to the native starch, and wherein said product is produced by a process comprising the steps of preparing an aqueous slurry of the insoluble native starch, incubating the slurry at a temperature from about 40° C. to less than 60° C. for a time from about 2 hours to about 4 hours with a debranching enzyme to hydrolyze at least some 1,6-glucosidic bonds of the native starch molecules, and isolating the insoluble resistant starch product from the aqueous slurry.

2. The resistant starch product of claim 1, wherein said native starch is selected from the group consisting of rice starch, potato starch, corn starch, wheat starch, barley starch, tapioca starch, sweet potato starch, cassava starch, arrowroot starch, sago starch, and oat starch.

3. The resistant starch product of claim 2, wherein said native starch is rice starch.

4. The resistant starch product of claim 1, wherein said native starch contains less than 30% amylose.

5. A food product comprising the resistant starch product of claim 1.

6. The resistant starch product of claim 1, wherein the time of incubation is about 4 hours.

* * * * *